(12) United States Patent
Hoser

(10) Patent No.: US 8,399,196 B2
(45) Date of Patent: Mar. 19, 2013

(54) NUCLEIC ACID SEQUENCING METHODS, KITS AND REAGENTS

(75) Inventor: Mark J. Hoser, Broadstairs (GB)

(73) Assignee: GeneForm Technologies Limited, Kent (GB)

( * ) Notice: Subject to any disclaimer, the term of this patent is extended or adjusted under 35 U.S.C. 154(b) by 2002 days.

(21) Appl. No.: 10/546,268

(22) PCT Filed: Feb. 20, 2004

(86) PCT No.: PCT/GB2004/000709
§ 371 (c)(1),
(2), (4) Date: Jul. 17, 2006

(87) PCT Pub. No.: WO2004/074503
PCT Pub. Date: Sep. 2, 2004

(65) Prior Publication Data
US 2007/0148645 A1    Jun. 28, 2007

(30) Foreign Application Priority Data

| | | |
|---|---|---|
| Feb. 21, 2003 | (GB) | 0303964.1 |
| Mar. 11, 2003 | (GB) | 0305525.8 |
| Mar. 18, 2003 | (GB) | 0306119.9 |
| Apr. 1, 2003 | (GB) | 0307515.7 |
| May 3, 2003 | (GB) | 0310294.4 |
| Jun. 13, 2003 | (GB) | 0313689.2 |
| Aug. 28, 2003 | (GB) | 0320157.1 |
| Sep. 23, 2003 | (GB) | 0322245.2 |
| Nov. 4, 2003 | (GB) | 0325657.5 |
| Dec. 16, 2003 | (GB) | 0329053.3 |

(51) Int. Cl.
*C12Q 1/68* (2006.01)
*C12P 19/34* (2006.01)
*C07P 21/04* (2012.01)

(52) U.S. Cl. .................. 435/6.12; 435/91.2; 536/24.3

(58) Field of Classification Search ............ 435/6, 91.2; 536/24.31, 24.32, 24.33
See application file for complete search history.

(56) References Cited

U.S. PATENT DOCUMENTS

| | | | |
|---|---|---|---|
| 7,166,478 B2 * | 1/2007 | Stavrianopoulos et al. | .. 436/544 |
| 2002/0160972 A1 | 10/2002 | Cook et al. | |
| 2006/0166203 A1* | 7/2006 | Tooke | ................. 435/6 |

FOREIGN PATENT DOCUMENTS

| | | |
|---|---|---|
| WO | WO 99/14226 | 3/1999 |
| WO | WO 00/50172 | 8/2000 |
| WO | WO 00/56748 | 9/2000 |
| WO | WO 00/70073 | 11/2000 |
| WO | WO 03/051901 | 6/2003 |

* cited by examiner

*Primary Examiner* — Prabha Chunduru
(74) *Attorney, Agent, or Firm* — Patrick J. Hagan; Dann, Dorfman, Herrell and Skillman, PC

(57) ABSTRACT

The present invention relates to nucleic acid sequencing methods, kits and reagents, and more particularly to methods of sequencing nucleic acid which employ a nucleic acid processing enzyme and one or more nucleotide analogues that are capable of binding to the active site of the enzyme and to complementary bases in the nucleic acid molecule being sequenced, but which are non-incorporable or inhibitors of the nucleic acid processing enzyme. In further aspects, the present invention relates to conjugates which comprise a deoxyribonucleotide triphosphates (DNTPs) or an analogue thereof linked to an intercalating dye.

29 Claims, 15 Drawing Sheets

Fig 1 Quencher based single molecule sequencing and SNP analysis.

Fig 2 FRET based single molecule sequencing and SNP analysis

FIG 3 Quencher based polymerase inhibitor assay.

Fig 4 FRET based single molecule Sequencing assay.

Fig 5 FRET based SNP analysis.

Fig 8 T.I.R.F apparatus for oligonucleotide assessment

Fig 9 Method using dideoxy terminated primer

Fig 11: Multiplexed Homogeneous liquid phase SNP analysis using standard fluorometers

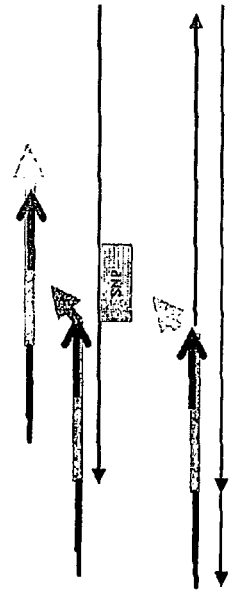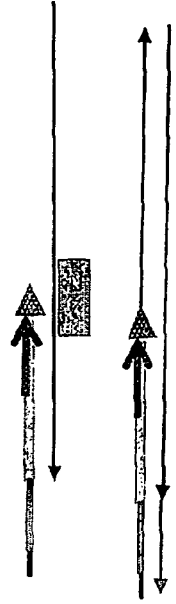
Figure 15

SEQUENCE LISTING

<160> NUMBER OF SEQ ID NOS: 6

<210> SEQ ID NO 1
<211> LENGTH: 51
<212> TYPE: DNA
<213> ORGANISM: Artificial Sequence
<220> FEATURE:
<223> OTHER INFORMATION: Synthetic Sequence

<400> SEQUENCE: 1
tgtcactcct gagcgacgaa tctgtagacc acttatccgt tgcctatgc t        51

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
agcataggca aacggataag tgg        23

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
agcataggca aacggataag t        21

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
agcataggca aacggataag tg        22

<210> SEQ ID NO 5
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 5
tcgttcattc        10

<210> SEQ ID NO 6
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 6
taaaaaccct ggga        14

NUCLEIC ACID SEQUENCING METHODS, KITS AND REAGENTS

FIELD OF THE INVENTION

The present invention relates to nucleic acid sequencing methods, kits and reagents, and more particularly to methods of sequencing nucleic acid which employ a nucleic acid processing enzyme and one or more nucleotide analogues that are capable of binding to the active site of the enzyme and to complementary bases in the nucleic acid molecule being sequenced, but which are non-incorporable or inhibitors of the nucleic acid processing enzyme. In further aspects, the present invention relates to conjugates which comprise a deoxyribonucleotide triphosphates (DNTPs) or an analogue thereof linked to an intercalating dye.

BACKGROUND OF THE INVENTION

The majority of sequencing technologies are based on the natural machinery that living cells use to copy DNA. A nucleic acid processing enzyme called a polymerase reads and then replicates the DNA that constitutes the human genome. DNA is composed of a sequence of the four individual nucleotide bases. The polymerase reads these nucleotide bases one at a time as it copies the DNA, thereby creating a new strand which is complementary to the original. The polymerase will utilise deoxyribose nucleotide triphosphates (DNTPs) or their analogues which are the constituents of DNA. These are initially in solution at high concentrations and are incorporated into the DNA by the action of the polymerase. In order to detect them, the nucleotides bases may be fluorescently labelled so that they are capable of producing a signal. However, there is a problem in that the incorporated label must be distinguished from those present on the DNTPs remaining in solution. The majority of sequencing technologies therefore rely on alteration of the copied bases, together with a degree of purification of the modified DNA, in order to visualise the DNTPs incorporated into nucleic acid strand produced by the polymerase. This process dramatically increases the complexity of a technology and reduces its robustness or reliability, for example as compared with a homogeneous systems that did not depend on any manipulation of this sort.

This process forms the basis of the highly heterogeneous Sanger technique which utilises fluorescent chain terminators and electrophoretic separation of the product. The incorporation of modified bases also forms the bases for the majority of massive parallel approaches, see WO 93/21340 and U.S. Pat. No. 5,552,278. Unfortunately, when many nucleotide bases have been incorporated into the DNA, the total signal becomes overwhelming and it becomes impossible to detect the signal as a new base is added to the growing strand against the background. Some technologies overcome this by removing the label from the DNA chain after reading and before adding a new base. This is a lengthy and demanding process. There are several variants of this approach, but all demand numerous steps to analyse a length of DNA.

It is also important to understand that in such sequencing methods, the signal comes only from the most recently added bases and generally takes advantage of a phenomenon known as fluorescence resonance energy transfer (FRET). In this process, the polymerase is labelled with a fluorescent compound which captures the energy from the fluorescently labelled bases only if they are in very close proximity. Since the closest bases to the polymerase are those that have recently been copied, the sequence can be read during the polymerisation process without further manipulation.

In an example of this technique disclosed in WO 01/163751, the incorporation of labelled bases into an oligonucleotide is measured. There are numerous caveats to this approach since highly labelled oligonucleotides are difficult to produce. More importantly, there is a high degree of collisional fluorescence quenching between labels on the bases that have been added to the copied oligonucleotide. Furthermore, the signal from up to 20 bases will be captured and the signal strength from these labels is erratic due to the helical nature of the product. In a further approach, the gammaphosphate of nucleotide bases are labelled with an acceptor dye which is cleaved during nucleotide triphosphate incorporation (US Patent Application No: 2003-0064366). The system must be assessed at a high speed due to the natural rate of this reaction.

WO 97/45539 discloses the use of conjugates of a sequence recognizing element (SRE) covalently bound to a reporter group (RG). The reporter group may be an intercalating dye and the sequence recognizing agent is a peptide or a nucleic acid molecule comprising a series of bases or amino acids that is capable of interacting with a target sequence. Where a nucleic acid sequence is used, this application requires that it is sufficiently long to hybridise to a target molecule. Moreover, the only methods disclosed for the synthesis of these conjugates involve the synthesis of the sequence recognizing element with a functional group which is then capable of subsequent reaction to covalently bond to the reporter group.

It remains a problem in the art to develop new sequencing methods, kits and reagents, in particular those which are robust and capable of providing applications such as real time sequencing.

SUMMARY OF THE INVENTION

Broadly, the present invention relates to methods, kits and reagents suitable, inter alia, for sequencing nucleic acid molecules and detecting single nucleotide polymorphisms (SNPs). In some embodiments, the present invention concerns methods of sequencing nucleic acid which employ a nucleic acid processing enzyme and one or more nucleotide analogues that are capable of binding to the active site of the enzyme and binding to a complementary base in a nucleic acid molecule being sequences and which are non-incorporable or inhibitors of the nucleic acid processing enzyme. By way of example, this system may be employed for sequencing a template nucleic acid molecule, determining whether a template nucleic acid molecule comprises a single nucleotide polymorphism or determining whether a candidate compound is an inhibitor of the nucleic acid processing enzyme.

In further aspects, the present invention relates to deoxyribonucleotide triphosphates (DNTPs) or their analogues conjugated or linked to an intercalating or minor binding groove dye. These conjugates also negate a separation step since they are only fluorescent when in contact or incorporated into the DNA under investigation.

In some embodiment of the present invention, the limitations inherent in FRET based sequencing have been overcome by developing a FRET and fluorescent quenched based technology which does not rely on the incorporation of labelled bases into the growing oligonucleotide chain. The platform is based on the utilisation of nucleotide analogues which enter the active site of a polymerase when a specific base on the DNA template is about to be copied, but are not incorporated into the new strand which continues to be synthesised from natural nucleotides. Introducing inhibitors of this type which are fluorescently labelled, together with native nucleotides, makes FRET based sequencing a reality and provides a highly controllable homogeneous assay producing only natural products. Although the application of FRET allows substantial discrimination between nucleotides which are locally bound to the template DNA and those that are free, an extension of this approach is described here in which an intercalating dye is covalently attached to a nucleotide triphosphate (DNTP) or its non-incorporable analogue. The intercalating dyes are essentially non fluorescent when free in solution and only emit a fluorescent signal when physically in contact with DNA. Since the DNTP retains its capability to form base pairing in the presence of polymerase, the signal is dependent on the cognate template base which is being processed.

The hardware needed to assess this technology is available and allows at least 1 million individual molecules to be read in parallel but independently by processes such as Total Internal Reflection Fluorescence (TIRF) microscopy. Due to the inherent nature of the inhibitor based system, the process can be read slowly as the rate of de novo base incorporation into the oligonucleotide being sequenced can be reduced by increasing the inhibitor:native base ratio.

Accordingly, in a first aspect, the present invention provides a method for determining the sequence of one or more nucleic acid bases of a nucleic acid template molecule, wherein the bases are downstream of a 3' terminus of a primer which is annealed to the template forming a template-primer complex, the method comprising:
 (a) contacting the template-primer complex with (i) a nucleic acid processing enzyme capable of binding to the complex and extending the primer and (ii) one or more inhibitors of the nucleic acid processing enzyme, wherein the inhibitors are non-incorporable nucleotide analogues,
so that a non-incorporable nucleotide analogue which is complementary to the downstream base of the template molecule binds to the nucleic acid processing enzyme; and
 (b) determining the identity of the non-incorporable nucleotide analogue and hence the sequence of the complementary base in the template nucleic acid molecule.

Thus, in this aspect of the present invention, the sequencing employs the fact that a nucleic acid processing enzyme, such as a polymerase, is capable of recognising the correct next base in the sequence of a template nucleic acid molecule. Typically, this will be because the correct next base/nucleotide triphosphate has a stronger affinity for the enzyme-template-primer complex and/or the correct next base/nucleotide triphosphate will increase the affinity of the polymerase to the template-primer complex.

Generally, in this aspect of the invention, the method comprises the sequential determination of one or more nucleic acid bases on a nucleic acid molecule (DNA) such as the next template base(s) downstream of the 3' terminus of a primer in a template-primer complex by determining the binding of a nucleic acid processing enzyme such as a polymerase in complex with a non-incorporable molecular entity (inhibitor) to the nucleic acid and determining the nature of the base to be assessed by measuring the change in affinity of one or more of the enzyme inhibitor moieties within the enzyme-inhibitor-DNA complex, wherein:
 (a) the binding of the inhibitor to the enzyme alters the affinity of enzyme towards the template-primer dependent on the nucleic acid base to be assessed;
 (b) the binding of the template-primer to the enzyme alters the affinity of the enzyme towards the inhibitor dependent on the nucleic acid base to be assessed.

One application of this method of the present invention is for the sequencing of a nucleic acid template molecule by repeating the method to identify successive nucleotides in a nucleic acid template molecule. Conveniently, this can be achieved by using the non-incorporable nucleotide analogues in combination with incorporable (e.g. native) nucleotides, thereby allowing the enzyme to extend the primer when it binds to an incorporable nucleotide and so move along the template reading successive nucleotides in the nucleic acid template. Preferably, the method has the capacity for "real time" sequencing by using the non-incorporable nucleotide analogues and incorporable nucleotides in a ratio that enables sequential reading of successive nucleotides in the template using the non-incorporable nucleotide analogues and stepwise extension of the primer using the incorporable nucleotides. This may be adjusted by experimentation to balance the time taken by the system used for detecting the identity the non-incorporable nucleotide analogue to provide a detectable signal with the average time taken for the extension of the primer by incorporation of a nucleotide. The rate of polymerisation may also be controlled by altering the concentration of the non-incorporable inhibitor or by other inhibitors or by utilising an enzyme whose processivity can be altered by other means.

In a further application, the method may be used for determining whether a specific complementary nucleotide, e.g. a single nucleotide polymorphism (SNP), is present in a template nucleic acid molecule, by selecting a primer which binds to the template upstream of a site of the SNP and determining the identity of the nucleotide at the site of the SNP.

In a still further application, the method may be used for screening candidate compounds to determine their affinity for the nucleic acid processing enzyme. The candidate compound may be a candidate non-incorporable nucleotide analogue. In one example, this may comprise contacting the enzyme-template-primer complex and the non-incorporable nucleotide analogues with one or more candidate inhibitors and determining whether one or more of the candidate inhibitors is an inhibitor of the enzyme or of the formation of enzyme-template-primer complex.

Preferably, the step of determining the identity of the non-incorporable nucleotide analogue uses a label system having one or more components, wherein the components of the label system are associated with the non-incorporable nucleotide analogue and/or the nucleic acid processing enzyme and/or the enzyme-template-primer. In some applications, for example those involving sequencing of a portion of the nucleic acid template molecule, different non-incorporable nucleotide analogues may be labelled with distinguishable label systems. In some examples, one of more components of the label system are directly conjugated to the non-incorporable nucleotide analogue(s) or the nucleic acid processing enzyme, while in others one of more components of the label system may be indirectly associated with the non-incorporable nucleotide analogue(s) or the nucleic acid processing enzyme. The use of fluorescent label systems is particularly preferred.

By way of example, the label system may be used to produce a detectable signal based on a change in frank fluorescence (FF), fluorescence resonance energy transfer (FRET), fluorescence quenching (FQu), time resolved fluorescence (TRF), a radioactive label proximity assay (RLPA), or Raman scatter (RS), surface enhanced Raman scatter (SERRS), fluorescent lifetime imaging microscopy (FLIM), fluorescence correlation spectroscopy (FCS), fluorescence intensity distribution analysis (FIDA), fluorescence polarization (FP), bioluminescence resonance energy transfer (BRET), chemiluminescence resonance energy transfer (CRET), surface enhanced Raman scatter (SERS), surface plasmon resonance (SPR) or total internal reflection fluorescence (TIRF). The use of these detection systems and labels are discussed further below. These label systems may be employed in all aspects of the invention.

In one embodiment, the components of the label system comprise a fluorescent label and a fluorescent quencher. The underlying concept involved in this type of label system is that when the label and quencher are in close proximity, the presence of the quencher reduces the signal produced by the fluorescent label. For example, the method may employ a label system in which a fluorescent label is associated with the nucleic acid processing enzyme so that a detectable signal is produced when the enzyme is bound to the nucleic acid primer-template complex whereas fluorescent quenchers are associated with three of the four non-incorporable nucleotide analogues, so that the binding of the fourth, non-quencher labelled non-incorporable nucleotide analogues produces the detectable signal. Fluorescent labels are discussed extensively herein and any of these dyes may be suitable for use in this type of label system. Examples of fluorescent quencher dyes include methyl-red, N,N,N',Nt-tetramethyl-6-carboxyrhodamine (TAMRA), TMR QSY-7 DABCYL, Elle-Quencher™, Eclipse Dark Quencher, desferrioxamine and other iron containing compounds, black hole quenchers (QHB) or a charge transfer quenchers.

In one embodiment, the components of the label system comprise a donor fluorophore and an acceptor fluorophore. The underlying concept involved in this type of label system is that a distinguishable signal is produced when the donor and acceptor fluorphores are in sufficiently close proximity to allow the transfer of energy from the donor to the acceptor. Preferably, the donor fluorophore is associated with the nucleic acid processing enzyme and acceptor fluorophores are associated with the non-incorporable nucleotide analogues so that a detectable signal is produced when a non-incorporable nucleotide analogue binds to the enzyme-primer-template complex. Conveniently, different non-incorporable nucleotide analogues may have different acceptor fluorophores so that they are capable of producing distinguishable detectable signals.

Examples of suitable fluorescent donor fluorophores are a green fluorescent protein (GFP), a quantum dot, an intercalating dye, a minor groove binder dye or major groove binder dye, or fluorescent chemical entities such as fluorescein, rhodamine, phycoerythrin, BODIPY, DAPI (4',6-diamidino-2-phenylindole), Indo-1, coumarin, dansyl or cyanine dyes. Conveniently, the donor fluorophore is capable of absorbing radiation having a wavelength between about 300 to 900 nm, more preferably between about 350 to 800 nm, and is capable of transferring energy to the acceptor fluorophore.

Preferably, the acceptor fluorophore is capable of absorbing radiation having a wavelength between about 400 to 900 nm, more preferably between about 500 to 800 nm, and which have an excitation spectra overlapping with the emission of the donor fluorophore, such that energy emitted by the donor can excite the acceptor. Preferably, the acceptor fluorophore absorbs light at a wavelength which is at least 10 nm higher, and more preferably at least 20 nm higher, than the maximum absorbance wavelength of the donor fluorophore. Examples of suitable acceptor fluorophores are a rhodamine, a fluorescein derivatives, a green fluorescent protein (GFP), BODIPY (4,4-difluoro-4-bora-3a,4a-diaza-s-indacene) or a cyanine dye. Preferred examples of acceptor fluorophores include 5-carboxyfluorescein (FAM), 2'7'-dimethoxy-4'5'-dichloro-6-carboxyfluorescein (JOE), N,N,N',Nt-tetramethyl-6-carboxyrhodamine (TAMRA), 6-carboxy-X-rhodamine (ROX), BODIPY or a cyanine dye. Depending on the application, some compounds are capable of acting as either a donor or an acceptor fluorophore.

In one embodiment, the components of the label system comprise a donor fluorophore which is an intercalating dye which is capable of binding to the double stranded nucleic acid formed when the template and primer nucleic acid sequences hybridise. Acceptor fluorophores associated with the non-incorporable nucleotide analogues can be used so that a detectable signal is produced when a non-incorporable nucleotide analogue binds to the enzyme-primer-template complex and are in proximity to the donor fluorophores. As in other embodiments of the invention, distinguishable detectable signals may be produced by different non-incorporable nucleotide analogues.

In a further embodiment, the components of the label system comprise one or more intercalating dye(s) covalently associated with or conjugated to one or more of the non-incorporable nucleotide analogues. The intercalating dye(s) are capable of producing a detectable signal when the non-incorporable nucleotide analogue binds to the enzyme-primer-template complex. Thus, in this embodiment, the proximity of the intercalating dye to the double stranded nucleic acid formed when the primer hybridises to the template nucleic acid molecule causes the production of a distinguishable signal. By suitable choice of labels, this can be used to identify the non-incorporable nucleotide analogue bound to the enzyme-primer-template complex and hence the identity of the complementary base in the template.

Examples of intercalating dyes that may be used in accordance with any appropriate aspects of the present invention include DNA binding monomeric or multimeric asymmetric cyanine or acridine dyes, for example in the form of reactive esters, examples of which include the Sybr family of intercalating dyes (Sybr-101; Molecular Probes Incorporated, USA); Propidium Iodide Thiazole orange, ethidium bromide, Ethidium monoazide PO-PRO, BO-PRO, YO-PRO; TO-PRO, JO-PRO, LO-PR and BO-PRO (as supplied by Molecular Probes, Oreg., USA) Hoechst 33258, Hoechst 33342 and Hoechst 34580, 4',6-diamidino-2-phenylindole, or 7-aminoactinomycin D (7-AAD), which demonstrates a spectral shift rather than enhancement when bound to double stranded DNA. In this and other aspects of the invention, the use of DNA binding monomeric or multimeric asymmetric cyanine or acridine dyes is preferred.

There is also the possibility of employing donor and acceptor fluorophores, where the donor fluorophore is placed on the nucleic acid under investigation and where the acceptor fluorphore is associated with the nucleic acid processing enzyme or one or more of the nucleotide analogues so that the acceptor fluorophore is excited or quenched by the donor fluorophore when both are in proximity through the formation of the enzyme-template-primer complex.

In a further embodiment, the label system comprises acceptor fluorophore which are Raman labels and donor fluorophores which are a Raman enhancers such as silver nanoparticles.

In some preferred embodiments of the invention, and especially those involving the sequencing of a nucleic acid template molecule, advantageously, the different non-incorporable nucleotide analogues are provided with distinguishable labels, for example where different non-incorporable nucleotide analogues are labelled with spectrally distinguishable acceptor dyes or intercalating dyes wherein the different labels are excitable by one species of donor dye.

In the present invention, "nucleic acid" includes single and double stranded nucleic acid, ribonucleic acid, and sequences comprising nucleotides which are modified as compared to native nucleotides, but which are capable of being processed in accordance with the present invention. Examples of such modified nucleotides include thioro-phosphate linked nucleotides or oligonucleotides with modified bases capable of sustaining Crick-Watson pairing during copying or processing.

In the present invention, "intercalating dye" includes intercalating dyes, minor groove binding dyes and major groove binding dyes. All of these entities bind to nucleic acids and, whereas, strictly speaking, intercalating dyes bind to the base (purine or pyrimidine) moieties of DNA, minor and major groove binders have affinities for the groove of dsDNA or the backbone of the nucleic acids. Many of the intercalating dyes described here demonstrate a mixed binding mode. In the context of this invention, the intercalating dye shows a preference for binding to dsDNA over that of ssDNA and generally fluoresces minimally in the presence of single stranded DNA or in the absence of DNA.

The nucleic acid processing enzyme used in accordance with the present invention is preferably a DNA polymerase. However, other enzymes, for example a reverse transcriptase, a RNA dependent polymerase, or a polymerase with exonuclease activity may also be used. In some embodiments, the nucleic acid processing enzyme may in addition to the properties described above also have primase activity, that it the ability to synthesizes a primer using the template and therefore not require the addition of exogenous primer.

In further embodiments of the invention, polymerase with either 3'-5' exonuclease activity or 5'-3' exonuclease activity may be used. In yet further embodiments of the invention, a polymerase is used that lacks all exonuclease activity. Polymerases lacking exonuclease activity are generally annotated as exo- and are available either intrinsically lacking exonuclease or as mutated forms of a polymerase that removes the said activity. Klenow-exo- and the exo-forms of vent and 90 North (New England Biolabs, USA). Examples of proof reading enzymes with 3'-5'exonuclese activity are Pfu polymerase (Stratagene, Calif.) and deep vent polymerase (New England Biolabs, USA). Proof reading activity may also be obtained by mixing any enzyme capable of proof reading such as the P53 protein (Eur J. Biochem. 2001 April; 268(7):2047-54. Exonucleolytic proof reading by p53 protein. Bakhanashvili M.) with a polymerase. A typical example of polymerase with 5'-3' exonuclease activity is Taq polymerase available form numerous sources and well know to those familiar with the art.

Generally speaking, components of the label system are associated with the non-incorporable nucleotide analogue and/or the nucleic acid processing enzyme and/or the enzyme-template-primer complex. Methods for achieving this are well known in the art and include chemical conjugation or by expression as a fusion protein where the label system and reagent it is conjugated to are both polypeptides. In some embodiments, the nucleic acid processing enzyme (e.g. a polymerase) may be covalently attached to the non-incorporable nucleotide analogue such that the affinity of the polymerase inhibitor conjugate to the nucleic acid substrate is dependent on the sequence of the substrate. This may lead to the enzyme being specific for a particular nucleotide analogue and, for example, may therefore be useful for the development of reagents for carrying our SNP analysis.

Examples of enzyme-nucleotide analogue conjugates include imidazolides of dNMP, 5'-fluorosulfonyl-benzoyldeoxy-adenosine (FSBdA), 8-azido-ATP or 5-azido-dUTP, 2,3,5,6-tetrafluoro-4-azidobenzoyl group (FAB-4-dUTP), (5-[N-(2,3,5,6-tetrafluoro-4-azidobenzoyl)-trans-3-aminopropenyl-1]- and 5-(N—[N-(4-azido-2,5-difluoro-3-chloropyridine-6-yl)-3-aminopropionyl]-trans-3-aminopropenyl-1)-2'-deoxyuridine 5'-triphosphates or pyridoxal 5'-phosphate (PLP).

In all applicable aspects of the present invention, examples of non-incorporable nucleotide analogues capable of sequence specific interaction with a template nucleic acid molecule include H2-HPUra, H2-HPIso or by 4-Hydroxy-17-methylincisterol, aphidicolin, 2',2'-difluorodeoxycytidine (gemcitabine), triphosphates of acyclovir (ACV), 1-(2'-deoxy-2'-fluoro-beta-D-arabinofuranosyl)-5-iodocytosine (FIAC) and E-5-(2-bromovinyl)-2'-deoxyuridine (BVdU), 2'-Fluoro-2'-deoxycytidine triphosphate, 3'-ethynylcytidine (ECyd), 1-beta-D-arabinofuranosylthymine 5'-triphosphate and 1-beta-D-arabinofuranosylcytosine 5'-triphosphate, 3'-amino-3'-deoxythymidine, 5'-triphosphates of (E)-5-(2-bromovinyl)-2'-deoxyuridine and (E)-5-(2-bromovinyl)-1-beta-D-arabinofuranosyluracil, 3'-azido-2',3'-dideoxy-E-5-styrylUTP (6) and 2',3'-dideoxy-E-5-styrylUTP, 1-(2-Deoxy-2-fluoro-beta-L-arabinofuranosyl)pyrimidine, E-5-(2-bromovinyl)-1-beta-D-arabinofuranosyluracil, thymidine 5'-[alpha,beta-imido]triphosphate, 4'-azidothymidine triphosphate, 5-(2-chloroethyl)-2'-deoxyuridine, R- and S-enantiomers of 9-(3,4-dihydroxybutyl)guanine [(R)- and (S)-DHBG], 9-(4-hydroxybutyl)guanine (HBG), and 9-(2-hydroxyethoxymethyl)guanine (ACV), 3-(substituted-butyl)-6-(3-ethyl-4-methylanilino)uracils, N2-(p-n-butylphenyl)dGTP (BuPdGTP) and 2-(p-n-butyl-anilino)dATP (BuAdATP), triphosphate derivatives of oxetanocin G, carbocyclic analogue of 2'-deoxyguanosine, ganciclovir, pyridoxal, pyridoxal-5'-mono-, di- and triphosphate, (S)-9-(3-hydroxy-2-phosphonylmethoxypropyl)adenine, 3'-O-methyl-ATP or nucleotide triphosphates which are made non-incorporable by alpha to beta phosphate methylene derivatisation. This latter class of analogues are preferred in the present invention.

In some embodiments of the present invention, it is preferred that the nucleotide analogue is intrinsically non-incorporable and does not become covalently bound to the primer. However, in other embodiments, a similar result can be produced by employing a nucleotide analogue which is a native deoxyribose nucleic acid triphosphate (dNTP) which is non-incorporable in that extension of the primer is inhibited. Conveniently, this can be achieved by capping the primer of the enzyme-primer-template complex so that incorporation of the next base is prevented. By way of example, the capping may be carried out by dideoxy-3' capping or temporary capping of the primer with a reversible terminator of elongation such as 3'-O-(2-nitrobenzyl)-dNTP modification of the primer.

The methods of the present invention may be carried out in solution or some of the reagents may be immobilised on a solid phase. In the latter case, preferably (a) the template nucleic acid molecule is immobilised on a solid phase or (b) the nucleic acid processing enzyme is immobilised on a solid phase, e.g. a plurality of nucleic acid template molecules or enzymes may be immobilised on the solid phase at spatially separated locations.

In carrying out the present invention, consecutive but similar bases, e.g. polyadenosine, present in the DNA may be assessed by measuring one or more of the following:
  (a) the total signal produced as a multiple of the signal produced by the assessment of a single base; and/or
  (b) the total time of fluorescence as a multiple of the time of fluorescence produced by a single base; and/or (c) the lack of the FRET effect when a native base enters the active site. For correct base entry the polymerase retains the base and this can be measure directly and the retention may be maintained by the addition of pyrophosphate analogues or any molecule capable of interfering with the off rate of the base during processing. Equally, polymerase mutations that reduce processivity by preferentially slowing down the incorporation/chemical cleavage step may be used. Processivity may be reduced for this purpose by the alteration in metal ion concentration; and/or (d) synthesising a number of potential labels which are distinguishable for each base. Two consecutive bases may signal different labels but the even where the bases are similar; and/or (e) re-sequencing an oligonucleotide a plurality of times and assessing the average time taken to read one type of base.

In some embodiments, the primer extending activity of the nucleic acid processing enzyme is controlled by the altering the concentration of the non-incorporable inhibitor or by other inhibitors or by utilising an enzyme whose processivity can be altered by other means.

In a further aspect, the present invention provides kits for carrying out the methods described herein. In one embodiment, the present invention provides a kit for use in a method of determining the sequence of one or more nucleic acid bases of a nucleic acid template molecule according to any one of the preceding claims, wherein the kit comprises:

(a) a primer for annealing to a nucleic acid template molecule;

(b) a nucleic acid processing enzyme capable of binding to the complex and extending the primer; and (c) one or more inhibitors of the nucleic acid processing enzyme, wherein the inhibitors are non-incorporable nucleotide analogues that are capable of binding to an enzyme-primer-template complex when an inhibitor is complementary to a downstream base of the template molecule;

wherein one or more of (a) and/or (b) and/or (c) is labelled with a label system having one or more components, wherein the components of the label system are associated with the non-incorporable nucleotide analogue and/or the nucleic acid processing enzyme and/or the enzyme-template-primer complex so that a distinguishable signal from the label system is capable of identifying the non-incorporable nucleotide analogue binding to the enzyme-primer-template complex and hence the sequence of the complementary base in the template nucleic acid molecule.

In a further aspect, the present invention provides conjugates which comprises a deoxyribonucleotide nucleotide triphosphate (DNTP) or a DNTP analogue and an intercalating dye, and compositions and kits which comprise one or more of these conjugates. Where the conjugates are included in kits, the kit may optionally include one or more primers and/or a nucleic acid processing enzyme for extending the primers and incorporating one or more deoxyribonucleotide nucleotide triphosphates (DNTP) or a DNTP analogues into the extended primer sequence. Unlike the conjugates disclosed in WO 97/45539, the conjugates of the present invention are formed from single DNTP or analogues and are not part of a longer DNA sequence. The conjugates are also distinguished from those disclosed in WO 97/45539 as they have substantially no affinity for a nucleic acid template in the absence of the nucleic acid processing enzyme.

In some instances, the DNTP or DNTP analogue may be incorporable into a nucleic acid primer of a template-primer complex being extended by a nucleic acid processing enzyme, although such conjugates may themselves chain terminators after the DNTP or DNTP analogue has been incorporated. This can conveniently be achieved where the chain terminator DNTP or DNTP analogue is an acyclo-DNTP or a dideoxy-DNTP or a 3'-OH modified DNTP, e.g. where the 3'-OH modified DNTP is an alkyl or epoxy derivative.

In other embodiments, the DNTP or DNTP analogue is non-incorporable into a nucleic acid primer being extended by a nucleic acid processing enzyme and, for example, may be used in the methods and kits described herein which employ non-incorporable nucleotide analogues.

A range of different intercalating dyes may be used to make the conjugates described herein and include, by way of example, a DNA binding monomeric or multimeric asymmetric cyanine or acridine dye, generally known as members of the Sybr family of dyes (e.g. Sybr-101) obtainable from Molecular Probes Incorporated, USA; propidium iodide thiazole orange; ethidium bromide; ethidium monoazide; PO-PRO, BO-PRO, YO-PRO, TO-PRO, JO-PRO, LO-PR, or BO-PRO obtainable from Molecular Probes, Oreg., USA; Hoechst 33258, Hoechst 33342 or Hoechst 34580; 4',6-diamidino-2-phenylindole or 7-aminoactinomycin D (7-AAD), which demonstrates a spectral shift, rather than enhancement in signal when bound to double stranded DNA.

The conjugates of the present invention have a variety of uses. In one aspect, the present invention provides the use of a conjugate of a deoxyribonucleotide nucleotide triphosphate (DNTP) or a DNTP analogue and an intercalating dye as disclosed herein for labelling a nucleic acid molecule in a template-primer complex by the action of a polymerase. Thus, the nucleic acid molecule is labelled with the deoxyribonucleotide nucleotide triphosphate (DNTP) or DNTP analogue by using a nucleic acid processing enzyme to extend the nucleic acid molecule or by using the nucleic acid molecule as a template and amplifying it using one or more primers, wherein the extension or amplification reactions are carried out in the presence of the labelled deoxyribonucleotide nucleotide triphosphates (DNTP) or DNTP analogues.

In a further aspect, the present invention provides the use of a deoxyribonucleotide nucleotide triphosphate (DNTP) or a DNTP analogue conjugated to an intercalating dye as disclosed herein for determining whether a template nucleic acid sequence comprises a specific complementary base in its sequence, e.g. whether a single nucleotide polymorphism (SNP) is present in the template. Broadly speaking, there are three preferred ways of using the conjugates disclosed herein to detect whether a specific complementary base is present in a template nucleic acid molecule, namely (1) by extending a primer to incorporate a conjugate at the site of the specific complementary base, (2) by using primers prelabelled towards the 3' end so that the conjugate in the primer is capable of hybridising to a complementary specific complementary base of a template and then using an enzyme having 3'-5' proof reading activity to remove the conjugate from primers which are not complementary and (3) using primers prelabelled towards the 5' end as probes with a further primer for extension towards the probe so that where the conjugate in the primer hybridises to the complementary specific complementary base it can be removed by enzyme having 5'-3' proof reading activity to remove the conjugate from primers which are not complementary.

In all of these embodiments, a plurality of conjugates comprising different DNTP or DNTP analogues that are complementary to different nucleotide bases may be used, the conjugates either being available to extend one or more primer(s) or pre-incorporated into the sequence of a primer so that the intercalating dyes of the different conjugates are capable of producing distinguishable signals.

The first embodiment of this aspect of the invention preferably employs a primer having a 3' end terminating one base upstream of the specific complementary base of the template nucleic acid sequence. This allows a single base extension of the primer by the conjugate to be used to determine the identity of the specific complementary base using the intercalating dye. In this embodiment of the invention, it is possible to use a conjugate comprising a DNTP or DNTP analogue representing a single nucleotide base and unlabelled chain terminating bases representing the other three nucleotide bases are added to eliminate further primer extension.

In the second embodiment of this aspect of the invention, the 3' terminus of the primer is labelled with a conjugate comprising the DNTP or DNTP analogue. A nucleic acid processing enzyme such as polymerase can be used which has 3'-5' proof reading activity and cleaves conjugates which are not complementary to the specific complementary base of the template. This allows the identity of the specific complementary base can be determined by detecting a signal from the intercalating dye of a conjugate in the primer which is complementary or non-complementary to the specific complementary base of the template. Advantageously, the signal is detectable without separating the need to separate bound from excised DNTP or DNTP analogue.

It is well known that increasing the number of mismatched bases between a primer and template greatly reduces their affinity for one another. This property may be used by making primers comprising one or more further bases which are non-complementary to the template can be used, the further non-complementary bases being upstream of the 3' terminus of the primer. This can help to facilitate the 3'-5' exonuclease activity of the proof reading polymerase, by making more than a single base towards the 3' terminus of the primer non complementary to the template molecule including the SNP. This may help to counteract the tendency for the intercalating dye of the conjugate to exert a stabilsing effect when the primer binds to a non cognate 3'base.

In the third embodiment of this aspect of the invention, the specific complementary base is at position corresponding to the 5' terminus of the primer. In this embodiment, the primer is used as a probe, and the method additionally employs (i) a further primer which binds to the template nucleic acid molecule at a sequence which is 5' upstream of the probe. There are two ways in which this can be used to produce a change in the detectable signal which is indicative of the identity of the specific complementary base. In the first way, (ii) a nucleic acid processing enzyme having 5'-3' exonuclease activity is used, so that when the further primer is extended to the probe, if the 5' terminus of the probe is complementary to the specific complementary base, the nucleic acid processing enzyme digests the probe causing a reduction in signal from the intercalating dye. This is caused because the digestion of the labelled probe starting from its 5' terminus removes portions of the primer which are capable of hybridising to the template molecule. This process will cause the digested, labelled probe to be released from the template the reduction in the fluorescent signal. However, mismatched probe will not be digested in this way and will continue to provide a detectable signal from the intercalating dye. In the second way, the primer is also used as a probe, but the (ii) a nucleic acid processing enzyme has 5'-3' exonuclease proof reading activity, so that when the further primer is extended to the probe, if the 5' terminus of the probe is non complementary to the specific complementary base, the nucleic acid processing enzyme digests the probe thereby causing a reduction in signal from the intercalating dye.

In a further aspect, the present invention provides a method of producing a primer for use in determining whether a template nucleic acid molecule comprises a specific complementary base, the method comprising:

obtaining a first primer having a 3' end which is capable of hybridising to a sequence of the template nucleic acid molecule such that the 3' terminus of the primer is one base upstream of the specific complementary base to be interrogated;

obtaining a second primer which is complementary to at least part of the sequence of the first primer and which has an overhang, e.g. a single base overhang, at its 5' end when hybridised to the first primer.

extending the first primer using a nucleic acid processing enzyme to incorporate a deoxyribonucleotide nucleotide triphosphate (DNTP) or a DNTP analogue which is conjugated to an intercalating dye at the position corresponding to the position of the specific complementary base in the template nucleic acid molecule.

In this aspect of the invention, the first and second primer may be joined by an intervening sequence of nucleic acid, e.g. so that they form a hairpin structure.

Preferably, the method further comprises using the enzyme to incorporate different deoxyribonucleotide nucleotide triphosphates (DNTP) or DNTP analogues in different primers at the position corresponding to the specific complementary base of the template. This can be used to produce a plurality of primers having different labelled nucleotides at positions corresponding to the position of the SNP in the template nucleic acid molecule. Conveniently, as in other aspects of the invention, the different primers may be labelled with different intercalating dyes, as disclosed herein. The method may also comprise the step of isolating the first primer. In the method, the second primer may conveniently comprise a 5' phosphate group that is capable of recognition and digestion by a lambda exonuclease.

In a further aspect, the present invention provides a method of determining whether a template nucleic acid molecule comprises a specific complementary base in its sequence, the method employing:

one or more primers comprising (i) a sequence which is complementary to a sequence of the template nucleic acid molecule flanking the single nucleotide polymorphism and (ii) a deoxyribonucleotide nucleotide triphosphate (DNTP) or a DNTP analogue conjugated to an intercalating dye at a position where it is capable of hybridising to the specific complementary base if it is complementary to the template at that position, the method comprising:

(a) contacting the template nucleic acid molecule with a nucleic acid processing enzyme and one or more of the primers under conditions, wherein the primer(s) are capable of hybridising to the template;

(b) detecting a signal from the intercalating dye produced when the DNTP or DNTP analogue is complementary to the specific complementary base;

wherein primers which are not complementary to the SNP do not produce a detectable signal because they do not hybridise to the nucleic acid template or if they do hybridise, the mismatched DTNP nucleotide is removed by a nucleic acid processing enzyme.

The method may employ a nucleic acid processing enyme having 3-5' exonuclease activity as described above.

In some embodiments, the DNTP or DNTP analogue is incorporable into a nucleic acid primer being extended by a nucleic acid processing enzyme. Alternatively, the DNTP or DNTP analogue may be non-incorporable into a nucleic acid primer being extended by a nucleic acid processing enzyme and is capable of binding to the nucleic acid processing enzyme when the DNTP or DNTP analogue is complementary to the next downstream base of a nucleic acid template molecule forming a complex with the primer.

In preferred embodiments, the method comprises determining the identity of a non-incorporable nucleotide analogue binding to the enzyme-template-primer complex by detecting the intercalating dye and hence determining the identity sequence of the specific complementary base in the template nucleic acid molecule.

In embodiments where the detection system comprises donor and acceptor fluorophores, the two components of the complex will be associated with a labelled entity; conversely, when an intercalating dye is associated with the nucleotide triphosphate analogue a second label is unnecessary since its binding to the template primer enzyme complex is intrinsically distinguishable from that which is unbound.

In embodiments using an intercalating dye conjugated to an incorporable DNTP or DNTP analogue or an incorporable DNTP analogue that is capable of chain termination, several methods may be used for detecting single nucleotide polymorphisms, see the discussion of the three preferred embodiments above. These methodologies take advantage of a single base extension of a primer template complex or 3'-5' exonuclease activity of the enzyme or 5'-3' exonuclease activity of the enzyme.

In a preferred method for single base extension detection of SNPs, the method is similar to that described previously, but with the inventive step that the system does not need to use standard fluorophores and can be measured without using frank fluorescence, rather than fluorescence polarization (Genome Research. Vol. 9, Issue 5, 492-498, May 1999 Fluorescence Polarization in Homogeneous Nucleic Acid Analysis Xiangning, Chen et al). Essentially, a primer is prepared which is complementary to the template under investigation and comprises a 3' terminus that is one base upstream of the template SNP site.

Where the template is the product of polymerase chain reaction (PCR) amplification, then it may be advantageous to remove the influence of one of the two product strands or one of the two primers used in the reaction. Where the nucleotide analogue conjugate does not compete adequately with the DNTPs intrinsic to the post PCR reaction mixture, then these may also be removed.

This can be achieved by utilising a 5'phosphate derivatised primer as one of the two primers in the PCR reaction. As a result, one of the two product strands will also have a 5' phosphate and this can be removed conveniently with a lambda exonuclease (N.E.B. USA) which preferentially degrades one strand of dsDNA in which the strand removed contains the 5' phosphate. Alternatively, the primers can be removed by utilising exonuclease-I (N.E.B. USA) which degrades single stranded DNA. In this latter case the primer used to assess the SNP must be added after the reaction.

In situations in which the intrinsic DNTPs are removed, this can be achieved with shrimp alkaline phosphatase (Promega®). The use of exonuclease-I and shrimp alkaline phosphatase together is described in U.S. Pat. Nos. 5,741,676 and 5,756,285. All reactants are utilised as described by the manufacturers and the system is heated to 70° C. for 10 mins after manipulations in order to destroy the enzymes.

Single base extension reaction used to assess the SNP can be performed as follows. The template and primer are mixed with an exo-polymerase such as Klenow exo- or the 9oN Archaeon polymerase Therminator (N.E.B, USA). Intercalating dye DNTP or DNTP analogue conjugate is added where:

(a) a single conjugate, cognate to a single base, is added together with native base which are chain terminators exemplifies by dideoxy- or acyclo-DNTPs cognate to the other three bases. The concentration of chain terminators will be high enough to be compatible with the polymerase and is generally 200 uM-1 mM;

(b) several conjugates each representing different bases and each conjugated to distinguishable intercalating dyes on binding to DsDNA. In this example, the conjugates are chain terminators since the intercalating dye is bound to dideoxy or acyclo-nucleotide triphosphates or similar analogues which generally rely on 3' hydroxyl modification.

The invention may also take advantage of 3'-5' proof reading exonuclease activity. This process is similar to that described previously (Genome Research; Vol. 13, Issue 5, 925-931, May 2003 Exo-Proof reading, A Versatile SNP Scoring Technology, Patrick Cahill et al), but intercalating dye-DNTP conjugates are used instead of standard fluorophore which allows for a homogenous system which can be read by frank fluorescence. Essentially, a primer is prepared that comprises an intercalating dye conjugated to the base at its 3'-terminus. The primer 3' terminus is opposite the template SNP under investigation. Where the label is not complementary to the template then it is excised by a proof reading polymerase of another enzyme possessing 3'-5' exonuclease proof reading activity, whereas if the base-conjugate is complementary to the SNP then it is retained during chain extension.

The primer may be prepared by chemical synthesis but may be conveniently prepared by the addition of the intercalating dye-DNTP conjugate using the action of a polymerase. This process takes advantage of the promiscuous nature of the 9°North polymerase when incorporating intercalating-dyes conjugated to DNTPs in the absence of native DNTPs. This process is described in detail below by way of an example below. Essentially, the primer used is hybridised to a second nucleic acid that has a complementary region to the primer and has a single base overhang at the 3' terminus of the primer. An exo-polymerase such as the 9°North polymerase is added, together with the intercalating dye DNTP conjugate, which is incorporated irrespective of whether or not it is cognate to the complementary base. The complementary nucleic acid is synthesised with a 5' phosphate moiety and as such may be degraded and removed from the system by Lambda exonuclease. The exonuclease is then inactivated by heating the system to 70° C.

Alternatively, a hairpin structure as shown in FIG. 15 may be designed which comprises a single base overhang at the 3' terminus intrinsic to the molecule and by intramolecular bonds which are weaker than the bonds formed between the primer when it is added to the template. This is enabled by utilising a portion of the primer that is complementary to the template, but not self complementary, in a fashion similar to that defined for the design of scorpion probes. Nucleic Acids Res. 2001 Oct. 15; 29(20):E96. Duplex Scorpion primers in SNP analysis and FRET applications. Solinas A et al).

Embodiments of the present invention may also take advantage of 5'-3' exonuclease activity. This method is similar to that described for TaqMan probes (Applied Biosytems Incorporated and U.S. Pat. No. 5,723,591), but with the inventive step that the system does not rely on dual labelled probes and rather relies on changes in fluorescence when an intercalating dye is released from dsDNA. Essentially, a probe is created that has a five prime terminus opposite the SNP site of a template. The 3' terminus or any other base is labelled with the intercalating dye as described above. Where the template is copied by the action of a polymerase with 5'-3' exonuclease activity as a result of a primer upstream of the probe, then the probe will be degraded if the 5' terminus of the probe is cognate to the SNP. Where the probe is not cognate to the SNP, then it will be released, but will fluoresce when re-annealed to the template or any complementary nucleic acid added to the system.

It is also possible to perform the method using a 5'-3' proof reading enzyme such as human exonuclease 1. (J Biol. Chem. 2002 Apr. 12; 277(15):13302-11. 2002 Jan. 24. Human exonuclease I is required for 5' and 3' mismatch repair Genschel J et al). In this method, the 5' terminus of the probe is opposite to the template SNP. The 5'terminus is comprises the conjugated intercalating dye which is manufactured by chemical synthesis. Where the 5' terminus is cognate to the SNP then it is not cleaved, whereas if the terminus is mismatched it will be cleaved.

Embodiments of the present invention will now be described by way of example and not limitation with reference to the accompanying figures.

BRIEF DESCRIPTION OF THE FIGURES

FIG. 15 shows a scheme for SNP analysis using conjugates of the present invention in hairpin primers.

DETAILED DESCRIPTION

General Description of Several Embodiments

Figure 1:
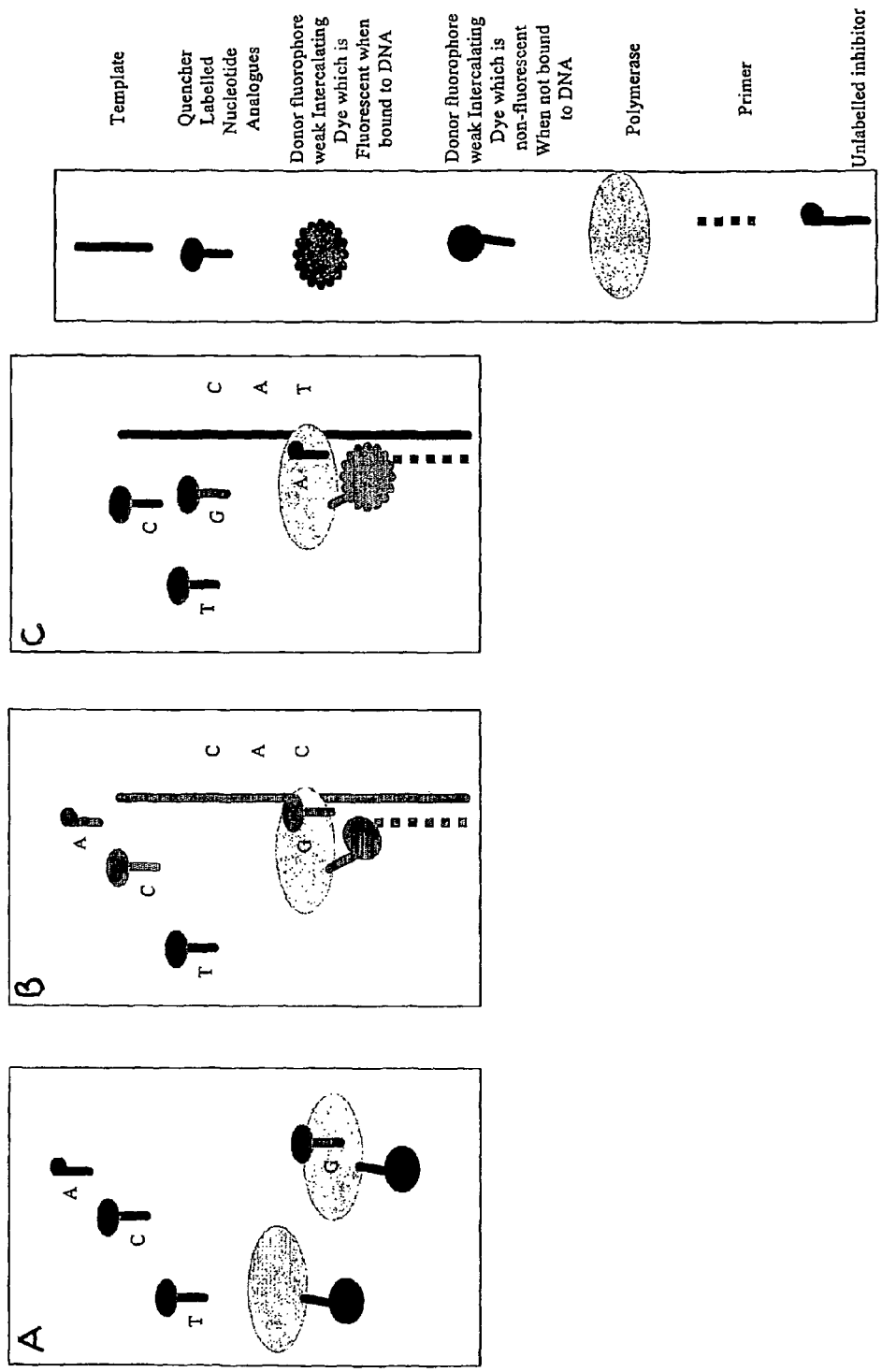
FIG. 1 shows a schematic of a quencher based single molecule sequencing and SNP analysis using non-incorporable template dependent inhibitors.

FIG. 1 shows a schematic of a quencher based single molecule sequencing and SNP analysis using non-incorporable template dependent inhibitors. In the embodiment of the invention shown in FIG. 1A non-incorporable template dependent inhibitors, such as those produced by derivation of alpha-beta phosphate bridging oxygen within DNTPs, are mixed with a nucleic acid processing enzyme, conveniently a polymerase. A rate limiting concentration of DNTPs may also be added and three of the four possible inhibitors are provided, each labelled with a fluorescence quencher. The polymerase is labelled with a weak intercalating dye which has little fluorescence and little affinity for DNA, but which provides a distinguishable fluorescent signal when forced into proximity with DNA, e.g. as formed between the nucleic acid primer and template. The entry of inhibitors into polymerase which is unbound, i.e. not part of an polymerase-primer-template complex, further reduces the fluorescence of the polymerase. In FIG. 1B, the mixture of added to a matrix bound template-primer complex. A quencher labelled non-incorporable inhibitor binds tightly to the active site of the polymerase DNA complex when it is complementary to the next base to be processed by the polymerase. This quenches the donor label intercalating dye bound to the polymerase which would otherwise fluoresce. Since fluorescence from the polymerase is quenched, photo bleaching is greatly reduced. However, FIG. 1C shows what happens when the non-quencher labelled inhibitor binds tightly to the active site of the polymerase DNA complex when it is complementary to the next base to be processed. This allows the donor label intercalating dye bound to the polymerase to fluoresce. After some time, the donor fluorescence may become bleached, but in that case, the polymerase dissociates from the complex and is replaced by another polymerase molecule. Native incorporable nucleotides may be added to the mixture so that they are sometimes added to the primer sequence by the polymerase, allowing the polymerase to move onto the next base of the template and thus allowing full sequencing. The molecule fluoresces for a period of time and with a total fluorescence output that is proportional to the number of consecutive bases of the type under assessment. The time between fluorescent events during which the donor fluorophore is quenched is proportional to the number of intervening bases.

Figure 2:
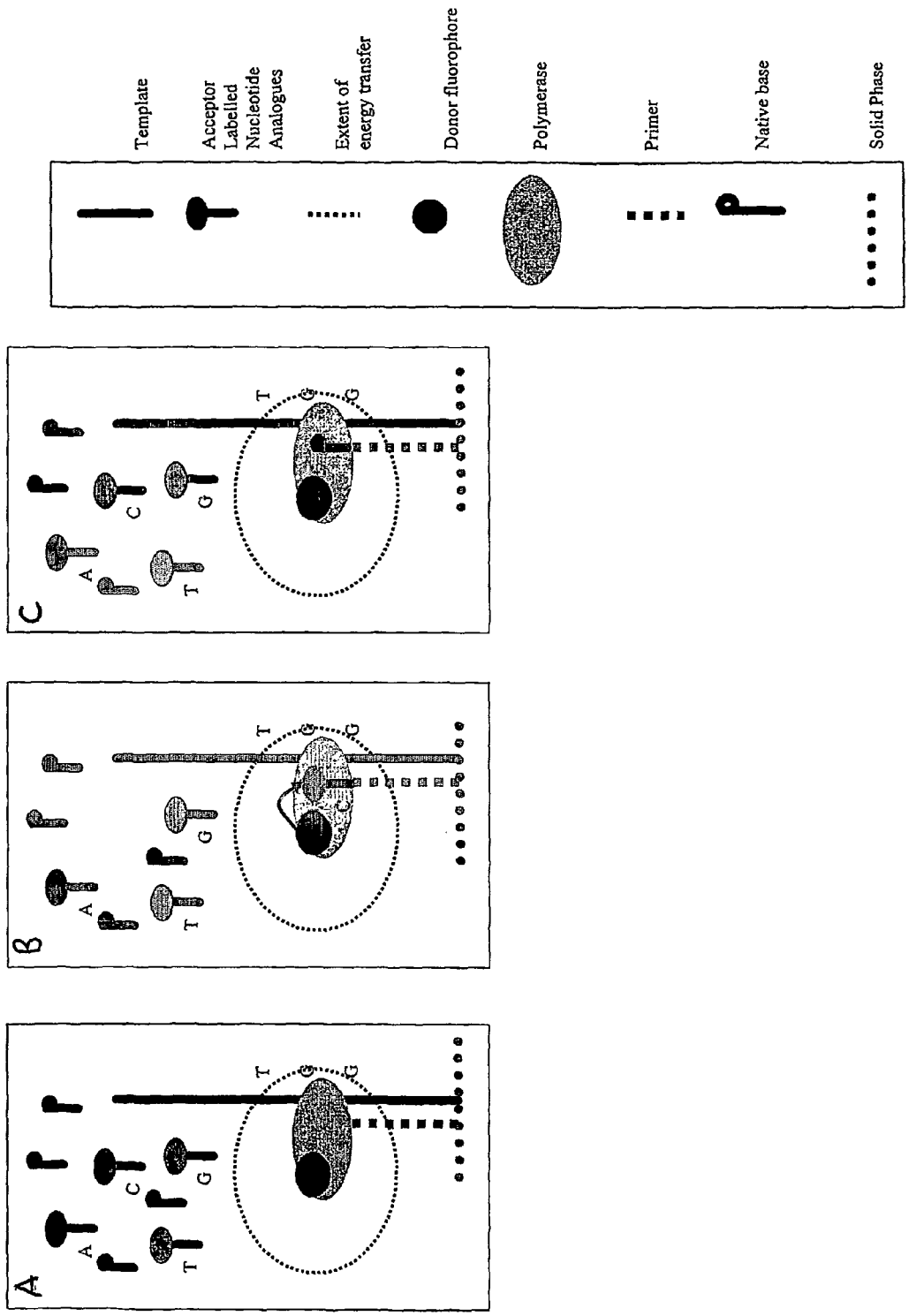
FIG. 2 shows a schematic of a FRET based single molecule sequencing and SNP analysis using acceptor labelled non-incorporable template dependent inhibitors and donor labelled polymerase.

FIG. 2 shows a FRET based single molecule sequencing and SNP analysis. In FIG. 2A, native bases are mixed with an excess of competitive non-incorporable nucleotide analogues which are inhibitors of the polymerase and which are labelled with acceptor fluorophore(s). This means that the labelled inhibitors are only detected when in the proximity of the active site of the polymerase which is also labelled, in this example with a donor fluorophore.

FIG. 2B shows the non-incorporable labelled inhibitor analogue of cytosine fits into the active site of the polymerase because the template that is being copied possesses a complementary guanidine nucleotide at the immediate downstream position. The binding of the cytosine inhibitor to the active site of the polymerase generates a fluorescent signal due to FRET and the sequence can be determined from the identity of the inhibitor. Since the labelled inhibitor cannot be incorporated it eventually leaves the active site and a native base is incorporated leaving the next template position to be sequenced, see FIG. 2C.

Figure 3:
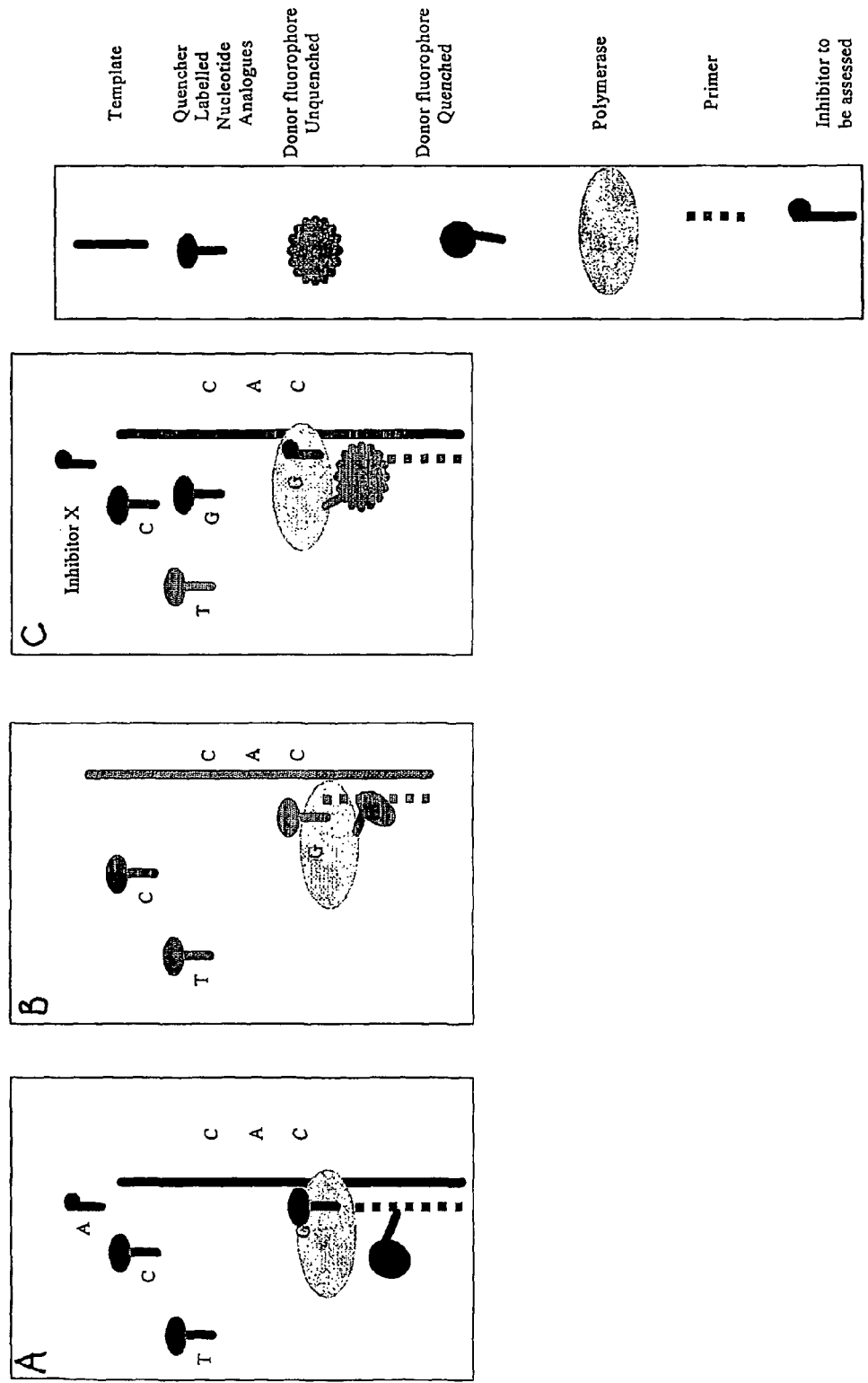
FIG. 3 shows a schematic of a quencher based polymerase inhibitor assay.

FIG. 3 shows a quencher based polymerase inhibitor assay for determining the affinity of an inhibitor (X) for the polymerase. FIG. 3A shows a polymerase and non-incorporable competitive polymerase inhibitors, having affinities which may be dependent or independent on nature the template base to be processed. Examples of such inhibitors include alpha-beta phosphate methylated nucleotide triphosphates. The polymerase and inhibitors are added to a template-primer complex labelled with a donor dye which can be quenched by the inhibitor labels. This means that the signal from the donor dye is quenched by the presence of the quencher labelled inhibitor in its active site (FIG. 3A). FIG. 3B shows an alternative arrangement in which the donor dye is conjugated directly to the polymerase and may be an intercalating dye which fluoresces when bound to DNA. However, the donor fluorophore is quenched by the presence of inhibitor in its inhibitor binding site. FIG. 3C shows that when an inhibitor X the affinity of which for the polymerase is the subject of the assay is added to the template-primer complex, the quencher present on the inhibitors is competitively displaced from the active site of the polymerase. As a result, fluorescence is increased proportional to the displacement of the quench-labelled inhibitor, thereby allowing the determination of the inhibitor X for the polymerase. Similarly, the polymerase will fluoresce directly in the scenario shown in FIG. 3B.

Figure 4:
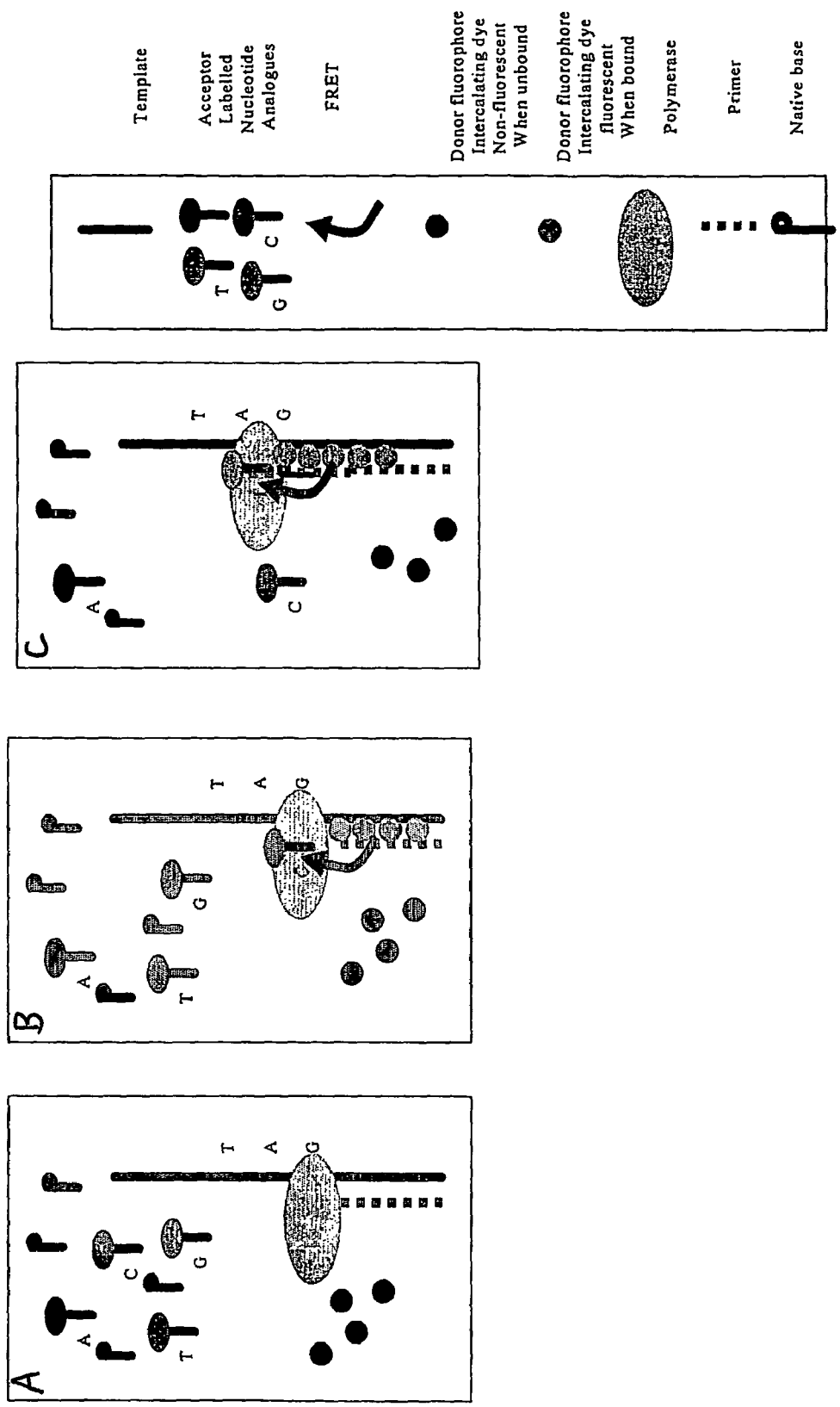
FIG. 4 shows a schematic of a FRET based single molecule sequencing assay and SNP analysis using intercalating dye as a donor molecule.

FIG. 4 shows a FRET based single molecule sequencing assay. In FIG. 4A, a small amount of native bases are mixed with an excess of labelled competitive non-incorporable nucleotide inhibitors. An intercalating dye is added as the donor fluorophore. In FIG. 4B, the non-incorporable labelled analogue of cytosine fits into the active site of the polymerase because that template that is being copied possesses a complementary guanidine nucleotide at the immediate downstream position. The signal from the nucleotide becomes detectable due to FRET and the sequence can be determined. In FIG. 4C, since the labelled inhibitor cannot be incorporated it eventually leaves the active site and a native base is incorporated leaving the next template position to be sequenced.

In another embodiment of the method shown in FIG. 4, the donor dye is the intercalating dye Sybr-green or a dye or quantum dot (Quantum Dot Corporation, USA) labelled to the polymerase. In this embodiment, a mixture fluorescent labelled reversible competitive non-incorporable base specific nucleotide inhibitors are added. The labelled non-incorporable base analogue is designed in such a way that each analogue binds to the polymerase in a fashion complementary to one of the four bases present as the next base to be processed on the oligonucleotide. The four inhibitors are each labelled with a different dye, all of which are able to absorb from the emission produced by the donor dye and are able to be distinguished FRET due to differential spectral properties. This may be performed by ensuring that the analogues have different emission wavelengths (such as Alexa dyes, Molecular Probes Incorporated, USA) which have the same absorption where the label on the polymerase is a donor) or by excitation at different wavelengths where the label on the polymerase is an acceptor. Alternatively, where the native analogue produces a distinguishable signal labelling is unnecessary.

The non-incorporated labels within the active site of the polymerase are determined by fluorescence resonance energy transfer and the base which is about to be assessed on the oligonucleotide can be determined because the active site of the polymerase favours the cognate inhibitor complementary to the template base. Clearly, in all embodiments utilising non-incorporable inhibitors, the polymerase is preferably utilised in molar excess over the templates that are being assessed.

In another embodiment of the invention where more than one base is to be determined and full sequencing is to be performed in a one step system (FIG. 4), the fluorescently labelled inhibitors detailed above are mixed with native bases. The concentration of native bases is adjusted so that they are incorporated into the oligonucleotide at a suboptimal rate and allow for fluorescent detection prior to their incorporation. Their rate of incorporation can also be reduced by adding pyrophosphate to the system.

Figure 6:
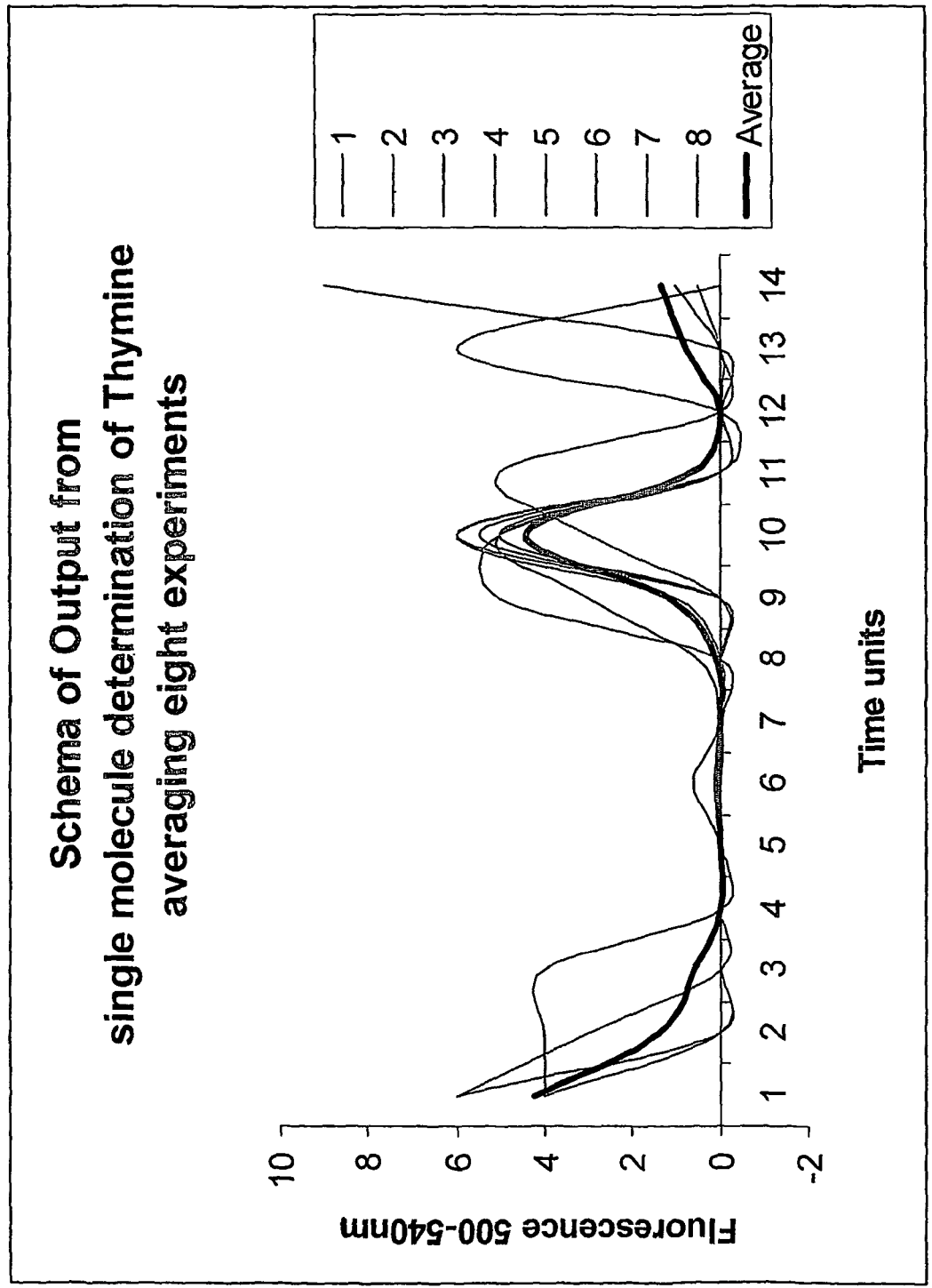
FIG. 6 shows a scheme of the output from a single molecule determination of thymine, showing fluorescence at 500-540 nm plotted against time and averaging several experiments.
Figure 7:
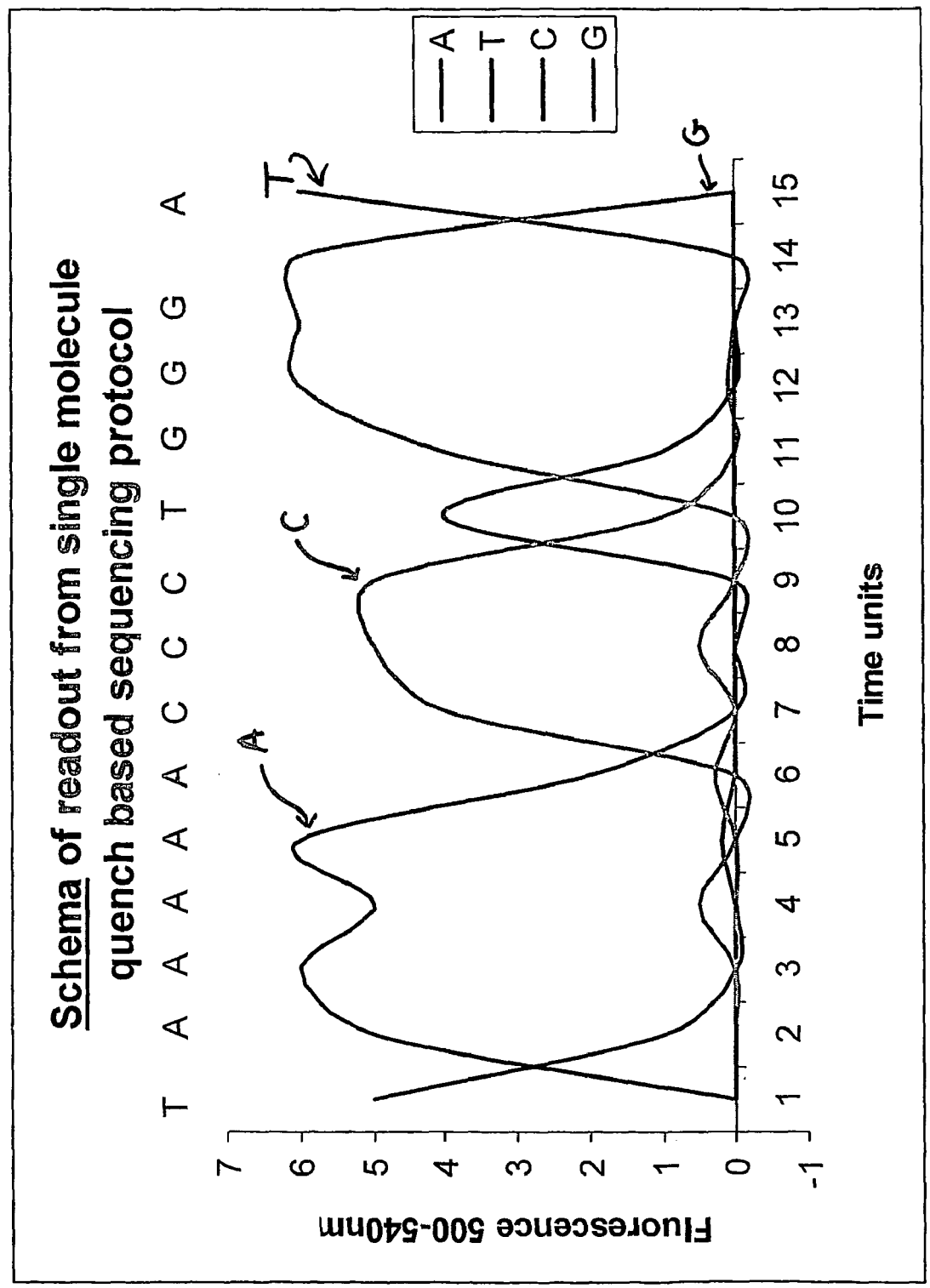
FIG. 7 shows a scheme of the output from a single molecule quench based sequencing protocol. The provided sequence is SEQ ID NO: 6.

After the oligonucleotide has been assessed, the system is regenerated by heating or by the use of chaotropic agents and the sequence can be re-read for the purpose of confirmation (FIG. 6). The system is washed and the process is repeated to determine one of the other four bases in a similar fashion. By assessing all four bases the combined output builds the full sequence of the oligonucleotide (FIGS. 6 and 7).

Figure 9:
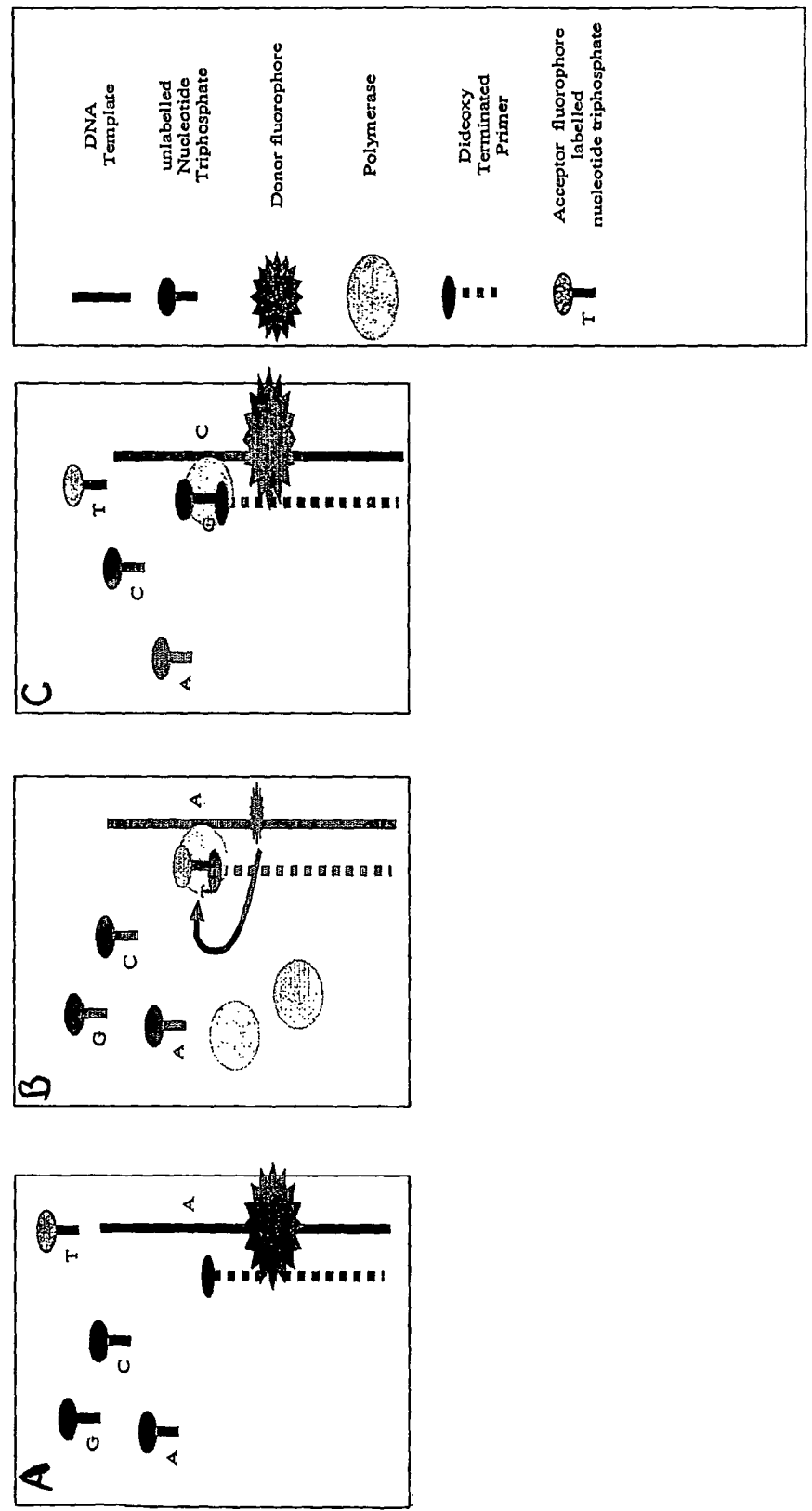
FIG. 9 shows a schematic of a method employing dideoxy terminated primer.

FIG. 9 shows a method in which a primer is capped by adding a dideoxy 31 terminus (see FIG. 9A). This stops incorporation of any further nucleotides by the action of polymerase. Standard nucleotides are added which are now non-incorporable. One of the nucleotides is labelled with a quencher dye. A DNA template which is complementary to the primer is added. The template is labelled with fluorescein which is close to the dideoxy terminus of the primer when the two when primer and template bind together. In FIG. 9B, a polymerase is added to the system and captures the nucleotide triphosphate which is complementary to the next template base to be copied. If the nucleotide is labelled with an acceptor dye then the dye comes into close proximity to the donor molecule. Excitation of the donor molecule causes energy to be transferred to the acceptor and subsequent quenching of the donor which can be measured. Where the next template base to be copied does not attract a cognate nucleotide which is conjugated to a quencher label then acceptor and donor are not placed in close proximity, see FIG. 9C. The acceptor dye will not be excited by the donor and will not emit at its emission wavelength.

Figure 10:
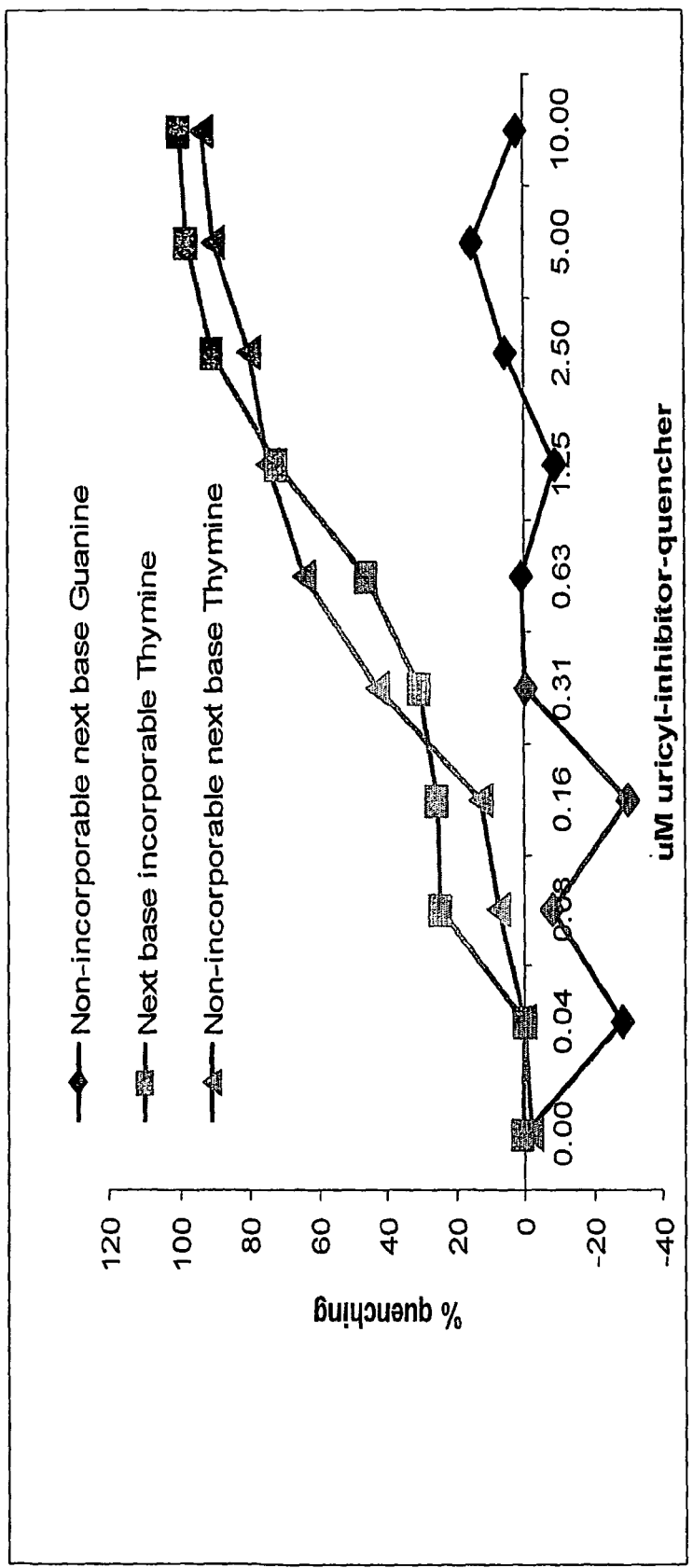
FIG. 10 shows the results from an experiment using the embodiment of the invention described schematically in FIG. 9.

FIG. 10 shows the results from an experiment using the embodiment of the invention described schematically in FIG. 9. A final volume of 10 ul contains 100 nM of the template and primer under investigation to determine the identity of the next consecutive base after the primer. Various quencher labelled inhibitors were used as shown in the figure. These included non-incorporable inhibitors or chain terminators, namely quencher (BHQ) labelled-DDUTP (incorporable) or BHQ-alpha-beta methylene-DUTP. The experiment was able to probe whether the next base of the template was a thymine or guanine. 300 nM Vent polymerase labelled with ROX was added with Sybr green, used according to the manufacturer's instructions. The system was heated to 50° C. and assessed at 620 nm. The system was not quenched when the next base to be sequences was not complementary to the quencher DNTP. The quenching could be reversed by addition of excess native DNTPs wherein the quencher was non-incorporable, but not where the DNTP was incorporable. All samples could be quenched by an excess of quencher labelled primer. The results show that the next base to be sequenced in the template was adenosine (see FIG. 9) as both incorporable and non-incorporable thymine led to quenching because it is complementary to the adenosine. On the other hand, non-incorporable guanine produced was not complementary and accordingly produced no quenching.

Figure 11:
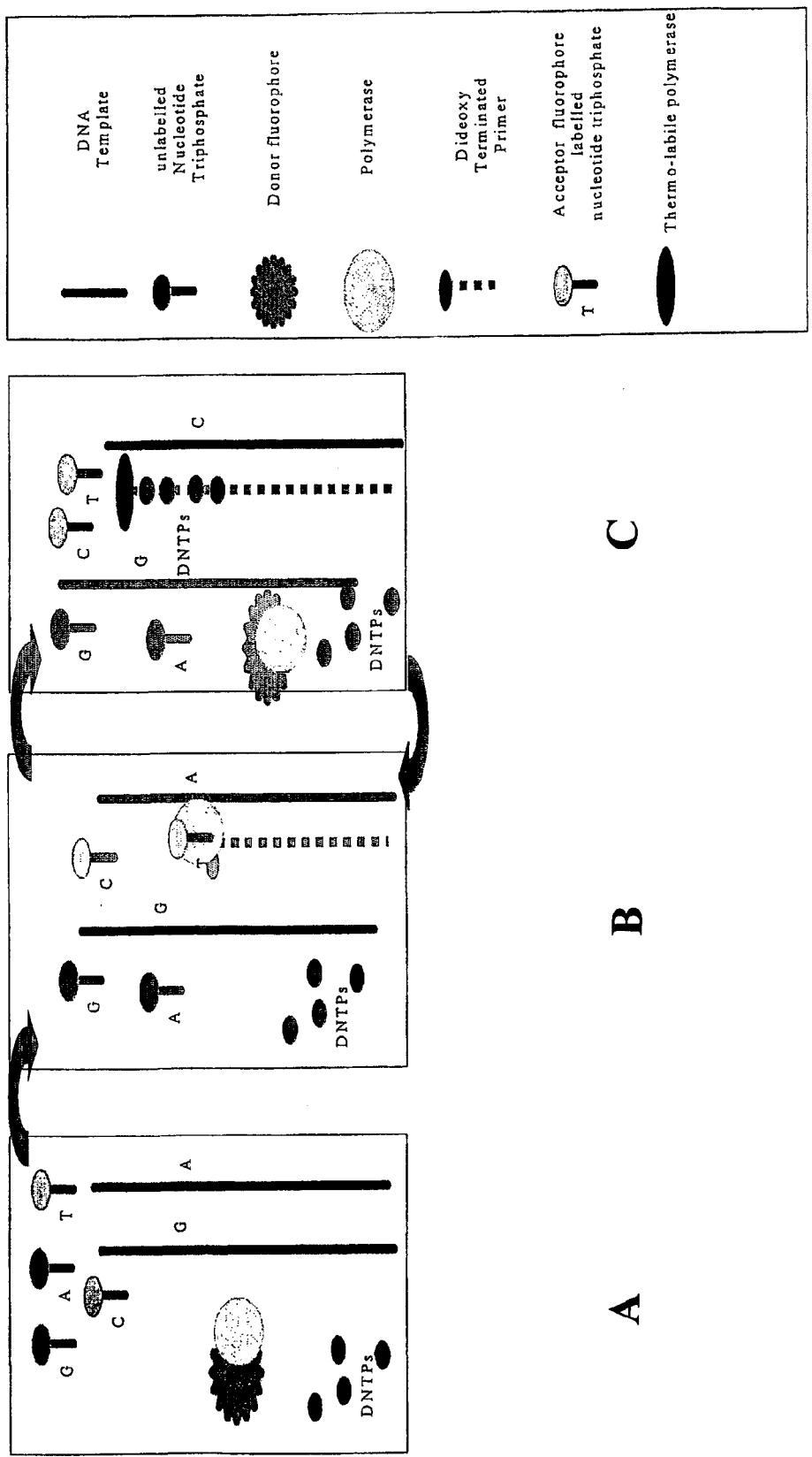
FIG. 11 shows a schematic of multiplexed homogeneous liquid phase SNP analysis using standard fluorescence.

FIG. 11 shows multiplexed homogeneous liquid phase SNP and analysis using standard fluorometers. In FIG. 11A, a sample DNA is subjected to multiplexed PCR using a polymerase friendly to modified nucleotides and driven to exhaustion of primer. Non-incorporable quencher labelled nucleotides are added to the mixture. In FIG. 11B, a limiting concentration of primer for the gene to be examined is added to the system. The system is maintained at high temperature and the nature of the nucleotide is determined by fluorescence quenching using any fluorometer capable of a single wavelength determination. The temperature of the system is then lowered and thermo-labile fluorescent labelled nucleotide unfriendly polymerase is added to the system such that the limiting concentration of primer is consumed (FIG. 11C). The temperature is raised and a second primer is added. Step 2 and 3 are recycled until all SNPs are decoded.

Figure 12:
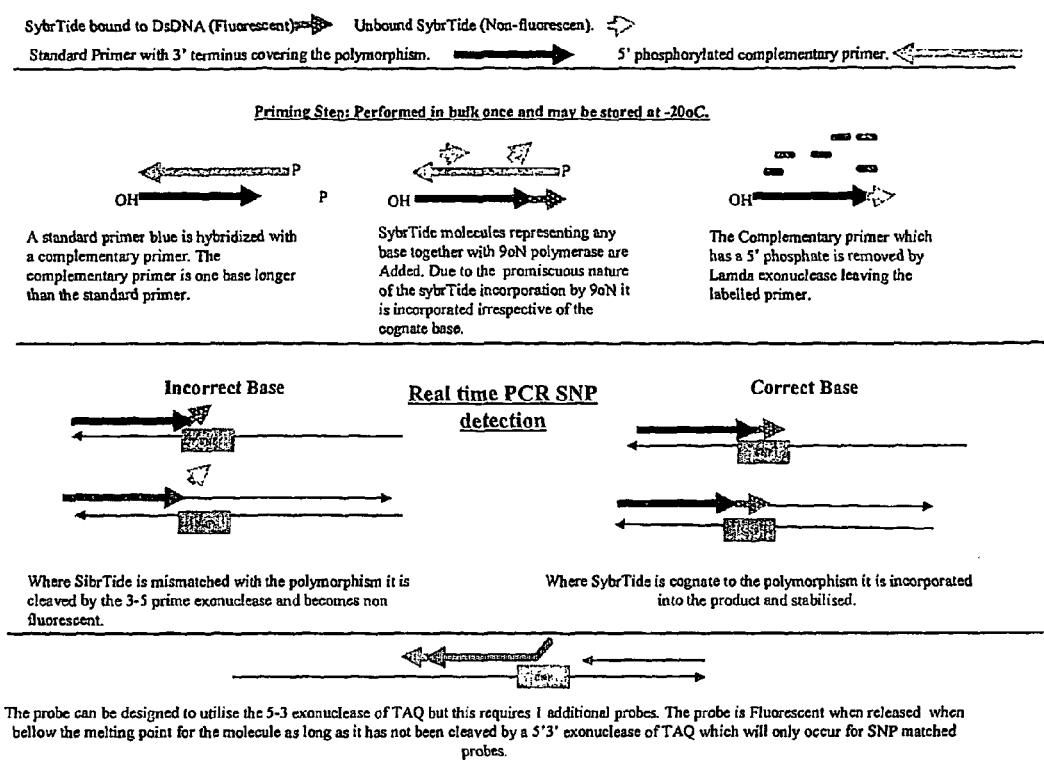
FIG. 12 shows the application of the invention for the determination of SNPs utilising the intercalate-nucleotide conjugate and taking advantage of the 3'-5' exonuclease activity of proof reading polymerases.

In FIG. 12 shows the application of the invention for the determination of SNPs utilising the intercalate-nucleotide conjugate. In the top portions of the figure, this takes advantage of the 3'-5' exonuclease activity of proof reading polymerases. A standard primer shown in dark print is designed so that its 3' terminus is one base upstream of the SNP that is being interrogated. This primer is hybridised with a complementary primer shown in lighter print. The complementary primer is one base longer at its 5' terminus than the standard primer. An intercalating dye conjugate and a nucleic acid processing enzyme such as 9oN polymerase, is added. Due to the promiscuous nature of the Sybr-Tide incorporation by 9oN in the absence of native DNTPs, the conjugates representing different bases can be incorporated irrespective of the complementary base on the complementary primer. Several intercalate-conjugates representing different bases and with different spectrally shifted dyes may be added to the system together or in separate reactions. In the final step, the complementary primer is removed because it has a 5'-phosphate group that is recognised and digested by an exonuclease such as lambda exonuclease. The primers may equally be prepared by incorporating the complementary regions into one molecule.

The use of these primers for detecting a specific complementary base such as a SNP in a template nucleic acid molecule is shown in the middle part of FIG. 12. Where the Sybr-Tide-DNTP analogue is mismatched with a polymorphism in the template, a proof reading nucleic acid processing enzyme such as 3-5 primer exonuclease cleaves the conjugate, removing it from proximity with the template-primer complex and causing a loss of fluorescence. However, when the Sybr-Tide conjugate in the primer is cognate to the polymorphism, it is stabilised and can emit a fluorescent signal. The final panel of FIG. 12 shows that the probe can be designed to utilise the 3'-5' exonuclease of TAQ, but that this requires an additional probe The probe retains its fluorescent properties when released below the melting point for the molecule as long as it has not been cleaved by 5'-3' exonuclease which will only occur for SNP matched probes in a similar manner to that described for TaqMan probes supplied by Applied Biosystems Incorporated, a technology well known to those skilled in the art, but without the need for dual labelled probes. In summary, the method uses a probe labelled with a conjugate as above and having a base at the 5' end of probe which may or may not be complementary to a SNP present in the template. As above a variety of probes specific for different possible bases at the SNP site may be used, e.g. if they are labelled with distinguishable intercalating dyes. The method uses a primer which binds to the template upstream of the conjugate labelled probe and is extended toward it by a polymerase. If the 5'end of the probe with the base corresponding to the SNP is complementary to it, the 5'-3' exonuclease activity of the polymerase will digest the probe and lead to the release of the conjugate and a loss of fluorescence. On the other hand, if the 5'end of the probe with the base corresponding to the SNP is not complementary, then it is not digested by the action of the polymerase, and the probe can rehybridise to further template molecules, thereby maintaining fluorescence.

Figure 13:
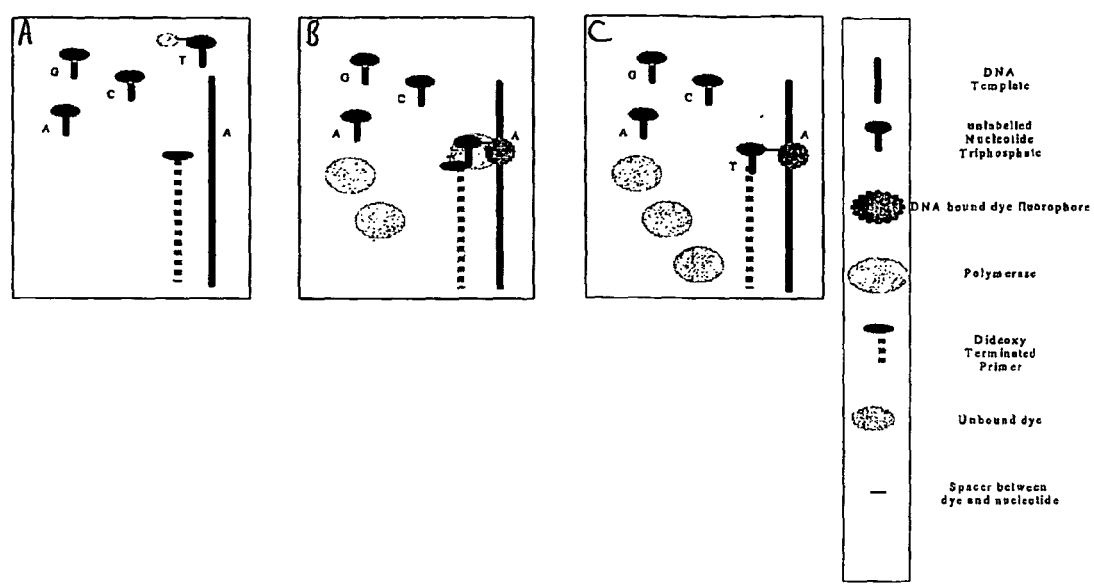
FIG. 13 shows a scheme using the conjugates of the present invention formed between an intercalating dye and a DNTP or DNTP analogue.

FIG. 13 shows a scheme using the conjugates of the present invention formed between an intercalating dye and a DNTP or DNTP analogue. In FIG. 13A, a primer is capped by adding a dideoxy 3' terminus which prevents further incorporation of nucleotides by the polymerase. Standard nucleotide can then be added to the system and are not incorporated to extend the primer. One of the nucleotides is labelled with the intercalating dye, i.e. is a conjugate according to the present invention, such as thiazole orange or Sybr green. When a template is present with the capped primer, the nucleic acid processing enzyme binds to the complex along with a nucleotide which is complementary to the next downstream nucleotide of the template, here an adenosine, see FIG. 13B. If the labelled conjugate binds to the complex then its spectral properties change and the nature of the next base can be confirmed. Where the primer is terminated by a 3' dideoxy cap then the conjugate will revert to the state in FIG. 13A if polymerase activity is abolished. If the primer is not terminated, then the single base is incorporated and the signal is stabilised as above. Where incorporation of a single base takes place further extension is inhibited since didoxyribonucleotide triphosphates are used.

Figure 14:
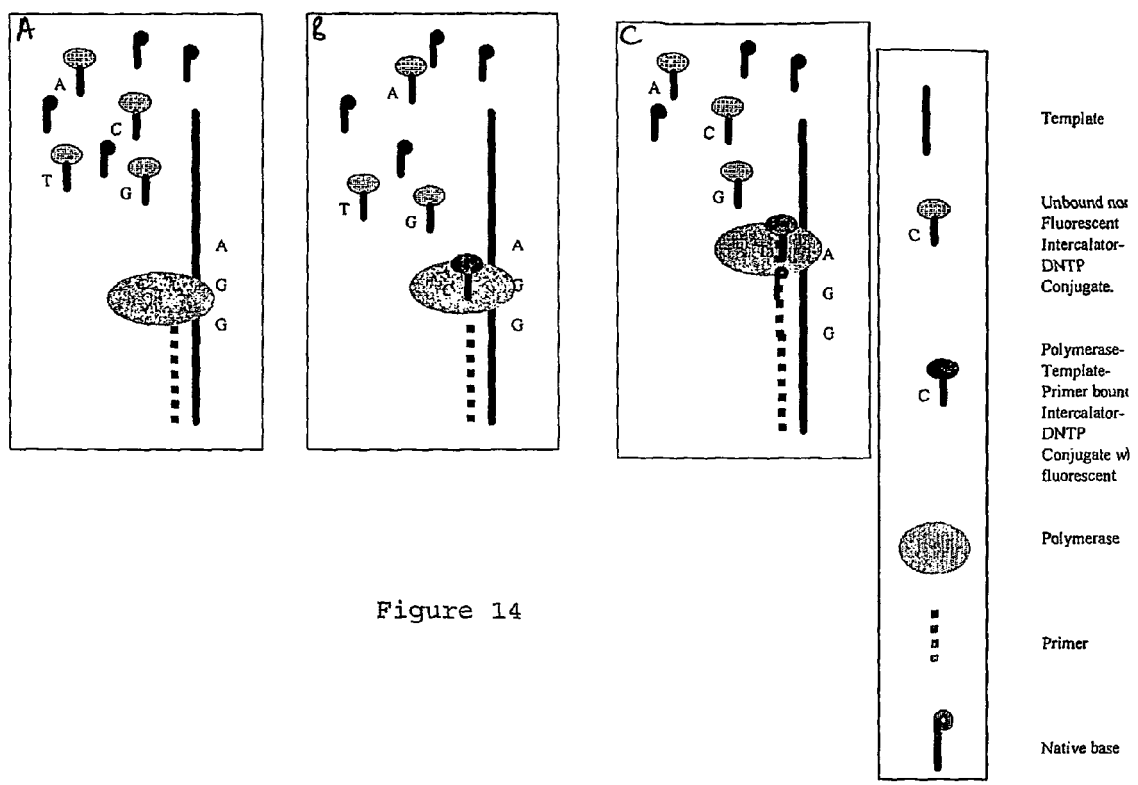
FIG. 14 shows a preferred method of how sequencing can be carried out using the conjugates of the present invention.

FIG. 14 shows a preferred method of how sequencing can be carried out using the conjugates of the present invention. In FIG. 14A, native nucleotides are mixed with an excess of conjugates of alpha-beta methyl DNTP which can compete with the native nucleotides but which are non-incorporable. Each nucleotide analogue representing a different base is labelled with an intercalator dye that fluoresces at a different wavelength when present in the nucleic acid processing enzyme-primer-template complex. In the FIG. 14B, the non-incorporable labelled nucleotide analogue of cytosine fits into the active site of the polymerase because the template that is being copied has a complementary guanidine at the position immediately downstream of the end of the primer. The signal from this nucleotide is detectable due to the increased fluorescence when the intercalating dye is bound to the complex. Since the labelled inhibitor cannot be incorporated into the extending primer, it eventually leaves the active site of the polymerase and a native base incorporated. This allows the system to move on and sequence the next nucleotide position in the template.

FIG. 15 shows an alternative to the method used in FIG. 12 which uses a hairpin or scorpion primer instead of two separate primers. The method works in just the same way as that described in respect of FIG. 12 except the two primers are complementary and form a hairpin when the first primer is extended to label the 3' end of that primer with a conjugate of a DNTP (or analogue) and an intercalating dye, such as Sybr Tide. Thus, the hairpin primer, Sybr Tide and Therminator polymerase are mixed in the absence of DNTPs. The Sybr Tide is incorporated efficiently regardless of whether it is cognate to the 5' terminus of the upper primer because of the promiscuous nature of this polymerase. In the PCR step in the lower left panel of FIG. 12, where Sybr Tide is mismatched with the polymorphism, it is cleaved by the 3'-5' exonuclease and the primer becomes non fluorescent. Any background from the melted probe is abolished by the exonuclease when the temperature is reduced at the end of the assay. In the lower, right panel where Sybr Tide is cognate to the polymorphism, it is incorporated into the product and stabilised and a fluorescent signal from the Sybr Tide molecule is observed.

Figure 5:
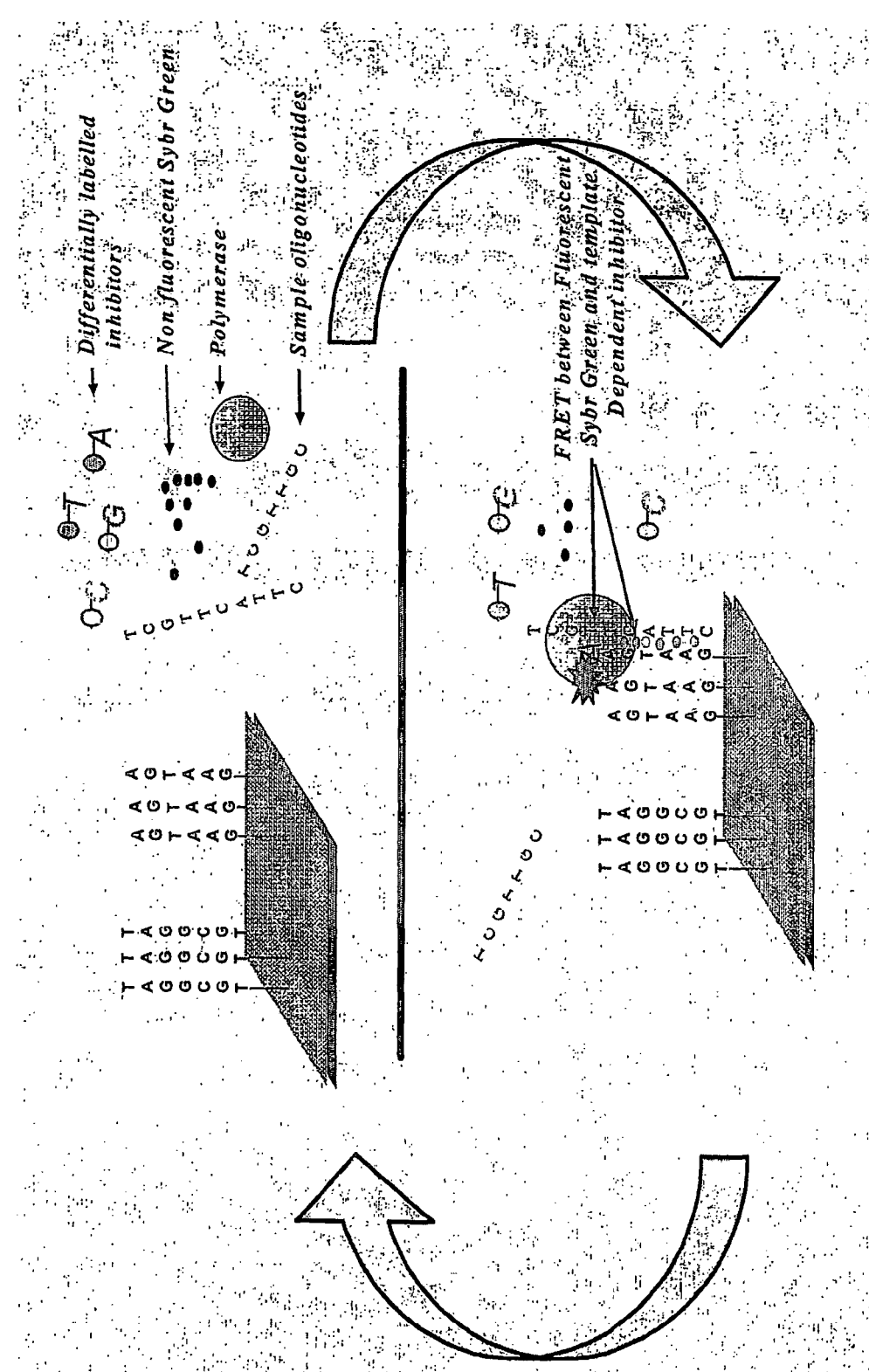
FIG. 5 is a diagram showing how FRET based SNP analysis according to the present invention works on a solid phase. The depicted 10-mer is SEQ ID NO: 5.

More generally, the methods of the present invention may employ a solid phase or surface to which single molecules of oligonucleotide may be attached at defined locations (FIG. 1) and/or where single molecules of different sequences are spread across the plate. Alternatively, the surface may comprise patches or areas of molecules at fixed positions on the plate or microarray, each patch represented by clones of identical molecules (FIG. 5). Alternatively, beads may be presented and each bead is coated with a molecules derived from a single oligonucleotide clone. In each case, the species attached to the solid phase may be the template nucleic acid molecule, the primer or the enzyme. The molecules may be covalently attached by their 3' terminus or non-covalently positioned with their 3' terminus in closest proximity to the surface by hybridising them to a primer molecule covalently attached to the matrix by its 5' terminus and has a sequence complementary to part of the oligonucleotide under investigation. Where the 3' end of the oligonucleotide is attached to the plate, the oligonucleotide is considered as a template for a polymerase and a primer complementary to a sequence on the oligonucleotide is added. It is feasible to utilise the 5' end of the oligonucleotide for attachment to the surface where the primer will be placed most distant to the surface and polymerisation will take place with elongation towards the matrix.

The oligonucleotide or primer may contain a spacer proximal to the surface and a region common to or complementary to all oligonucleotides from which chain elongation may take place after the complementary DNA is added. This requires that the oligonucleotides under investigation contain a common sequences which may be intrinsic to the population under investigation, for example as is the case for DNA reverse transcribed from mRNA comprising a poly-A tail, or it may be added by ligation of the common sequence by T4 RNA ligase (New England Biolabs, USA) as described by the manufacturer.

A donor fluorophore may be covalently attached to a polymerase (FIG. 2) or to the nucleic acid or non-covalently bound to the nucleic acid utilising intercalating dyes (See FIG. 4). Where the donor dye is attached to the polymerase it may be excitable directly by electromagnetic waves or may be designed to fluoresce only when the polymerase is in close proximity to or bound to the template-primer as is the case using the donor dye Sybr-101 (Molecular Probes Incorporated, USA) or another reactive intercalating dyes (FIGS. 1 and 3).

Alternatively, where single molecules are determined, the surface is assessed by suitable technologies such as by confocal and CCD instrumentation or TIRF (FIG. 8) for a signal induced by the binding of labelled polymerase to the oligonucleotide template-primer complex and may act to catalogue the positions and density of the oligonucleotides to be assessed. On the other hand, where patches of identical molecules are determined all analysis may be performed utilising commercially available microarray readers. In other embodiments of the invention in which molecules are assessed in bulk fluid phase then standard fluorometric readers are used.

In the aspects of the present invention that are concerned with sequencing one or more nucleic acid bases of a template or target nucleic acid molecule, the methods involve determining the nature of a non-incorporable template dependent inhibitor that binds to the active site of the polymerase and hence the identity of the base in the template strand being copied. Although native bases may be present in the system, they are incorporated slowly because of the excess of the non-incorporable template dependent inhibitor and this therefore allows the sequence of each base of the template to be determined in a stepwise manner, but without further manipulation of the system.

In one embodiment of the invention, the determination of the presence of an inhibitor in the active site of the polymerase relies on fluorescence quenching where the polymerase is conjugated to a fluorescent donor molecule and the inhibitor is conjugated to a quencher of fluorescence and is outlined in FIG. 1.

A particular quencher labelled inhibitor will preferentially enter the active site of the polymerase when its cognate base is being processed on the template molecule. Since it becomes intimately associated with the polymerase the fluorescence emission by the polymerase is reduced due to non radiative energy transfer. This quenching process is used to recognise the quality of the template base since it is cognate to the quencher labelled inhibitor.

Conversely, if an inhibitor that relays the presence of its cognate base is not in the active site then its cognate base is determined as not being the base processed by the polymerase.

Using these principles an embodiment of the principal is devised by which three of four possible inhibitors or a group of one or more inhibitors with cognition to three of the four bases are labelled with a fluorescence quencher that is able to quench the fluorescence of the donor dye within the polymerase. A fourth inhibitor cognate to the base to be identified is not labelled with a quench molecule.

Under these circumstances, when appropriate concentrations of inhibitors polymerase native base and template-primer complex are mixed then the system will only fluoresce when one particular base is present as the base being processed by the polymerase (FIG. 1).

Where native bases are absent then no incorporation will take place and the system in essentially static and will simply evaluate the next base downstream of the primer (FIG. 5).

The system will as a result of the disclosed method produce bursts of fluorescence with intervening absence of fluorescence. The total fluorescent output of a fluorescent burst and the total fluorescence time of a fluorescent burst will be directly proportional to the number of consecutive base of the type under investigation. Conversely, the duration of the absence of fluorescence by the donor will be directly proportional to the number of intervening bases representing those not under investigation. (FIGS. 6 and 7).

The system may be regenerated since the extended primer will dissociate from the template by raising the temperature above the melting temperature of extended complex or using chaotropic agents. The surface bound template may be washed under these conditions in order to remove other components such that the methodology can be repeated.

Where the system is regenerated methodology may be repeated in order to build a set of values which have reduced statistical variation and lie closer to the expected mean values (FIG. 6). The regenerated system may also be used to evaluate one or more of the other three bases in the oligonucleotide. (FIG. 7). In order to evaluate a complete sequence then a minimum of four repeated evaluations will be required.

The number of evaluations may be reduced by assessing more than one base at a time. This is exemplified by evaluation of (A and T) (A and C) (C and G). In this case each base will be represented uniquely within the experimental protocol. Equally inhibitors that have more than one cognate base may be used in this manner.

Conjugation or Attachment of Donor Fluorophore to a Polymerase

Donor fluorophores can be used by directly or indirectly attaching them to the polymerase. Amine-reactive fluorophores are frequently used to create fluorescently-labelled proteins. Examples of amine-reactive probes that can be used include reactive esters of fluorescein, BODIPY, Sybr101, rhodamine, Texas Red, and their derivatives (Molecular Probes Incorporated, USA). These dyes are capable of attaching to lysine residues within the polymerase, as well as to the free amine at the N-terminus. The reaction of amine-reactive fluorophores usually proceeds at pH values in the range of pH 7-10.

Alternatively, thiol-reactive probes can be used to generate a fluorescently-labelled polymerase. In proteins, thiol groups are present in cysteine residues. Reaction of fluorophores with thiols usually proceeds rapidly at or below room temperature (RT) in the physiological pH range (pH 6.5-8.0) to yield chemically stable thioesters. Examples of thiol-reactive probes that can be used include fluorescein, BODIPY, cumarin, rhodamine, Texas Red, and their derivatives.

Other functional groups on the protein that can be used for conjugating to fluorophores include alcohols, for example as present on serine, threonine, and tyrosine residues, carboxylic acids and glutamine, can be used to conjugate other fluorescent probes to the polymerase. Another fluorophore that can be attached to the polymerase is 4-[N-[(iodoacetoxy)ethyl]N-methylamino]-7-nitrobenz-2-oxa-1,3-diazole (IANBD), as described by Allen and Benkovic (Biochemistry, 1989, 28:9586).

Methods for labelling proteins with reactive dyes are well known to those well skilled in the art. In addition, the manufacturers of such fluorescent dyes, such as Molecular Probes (Eugene, Oreg.), provide instructions for carrying out such reactions.

In some embodiments of the invention, it is preferred that the fluorescently-labelled polymerases have a high fluorescence yield and retain the properties of the unlabelled polymerase, primarily the ability to synthesize a complementary strand of a nucleic acid molecule. However, under some circumstances it may be acceptable to employ a polymerase which has a less than maximal fluorescence yield, for example if this otherwise preserves the function of the polymerase.

The reactive groups may also be added to the polymerase by specific site directed mutation (Furey W S, Joyce C M et al Biochemistry. 1998 37:2979-90). Alternatively, the donor dye may be covalently attached to the nucleic acid or non-covalently bound to the nucleic acid utilising intercalating dyes (See FIG. 4) as described by the manufacturer (Molecular Probes). Where a donor dye is attached to the polymerase, it may be excitable directly by electromagnetic radiation or may be designed to fluoresce only when the polymerase is in close proximity to or bound to the template-primer as is the case using the donor dye that bind to DNA such as the reactive ester of thiazole orange or sybr-101 (supplied and described for conjugation by Molecular Probes) (FIGS. 1 and 3).

The polymerase will typically be one that is compatible with modified DNTPs (J Biotechnol. 2001 86; 237-53. Foldes-Papp Z et al) and lacks exonuclease activity where non-incorporable inhibitors are used, but is chosen on the basis of compatibility with cognate inhibitors. Examples of preferred polymerases include Sequenase and Thermose-queqnase (Amersham Biosciences), Therminator (New England Bioslabs) Klenow exo-(Amersham biosciences) and the Pol III family of polymerases. Following conjugation of the fluorophore to the polymerase, un-conjugated dye is removed, for example by gel filtration, dialysis or a combination of these methods.

Recombinant Green Fluorescent Protein-Polymerase

Green fluorescent protein (GFP) includes a chromophore formed by amino acids in the centre of the GFP. GFP is photostable which make it a desirable fluorophore to use on the polymerase because it is resistant to photobleaching during excitation. Wild-type GFP is excited at 393 nm or 476 nm to produce an emission at 508 run. However, GFP mutants are known in the art which have alternative excitation and emission spectra. One GFP mutant, H9-40 (Tsien, 1998, Ann. Rev. Biochem. 67:509; U.S. Pat. Nos. 5,625,048 and 5,777,079 to Tsien and Heim, herein incorporated by reference), has only a single absorption at 398 run and emits at 511 nm. A red-shifted GFP mutant RSGFP4 (Delagrave et al., Biotechnology 13:151-4, 1995) has an excitation at 490 nm and emission at 505 run. The blue-shifted GFP mutant BFP5 absorbs at 385 nm and emits at 450 nm (Mitra et al., Gene, 173:13-7, 1996).

The polymerase used for elongation of the primer strand can be attached to GFP to generate a fusion protein, GFP-polymerase, by recombinant techniques known to those skilled in the art. Methods for making fusion proteins are described in Sambrook et al. (Molecular Cloning, A Laboratory Manual, Cold Spring Harbor Laboratory, Cold Spring Harbor, N.Y., Chapter 17, 1989). Plasmids containing the wild-type or mutant GFP gene sequences and a multiple cloning site (MCS) into which the polymerase sequence can be inserted (i.e. pGFP), are available from Clontech (Palo Alto, Calif.). Briefly, both the polymerase DNA and the GFP plasmid are digested with the appropriate restriction enzyme(s) which allow for the insertion of the polymerase into the MCS of the GFP plasmid in the sense orientation. The resulting fragments are ligated and expressed in bacteria, such as E. coli. The expressed recombinant GFP-polymerase is then purified using methods known by those skilled in the art. The GFP molecule may be placed at the N- or C-terminus of the polymerase, or anywhere in between. The resulting GFP-polymerases are tested to determine which has the optimal properties for use in accordance with the present invention for sequencing. Such properties can include: ease of protein purification, amount of protein produced, amount of fluorescence signal emitted after excitation, minimal alteration of the fluorescent properties of the GFP.

The purification of recombinant fusion proteins has been made significantly easier by the use of affinity tags that can be genetically engineered at either the N- or C-terminus of recombinant proteins. Such tags can be attached to the GFP-polymerase protein, to aid in its purification and subsequent attachment to a substrate (see Example 2). Examples of affinity tags include histidine (His), streptavidin, S-tags, and glutathione-S-transferase (GST). Other tags known to those skilled in the art can also be used. In general, the affinity tags are placed at the N- or C-terminus of a protein. Commercially available vectors contain one or multiple affinity tags. These vectors can be used directly, or if desired, the sequences encoding the tag can be amplified from the vectors using PCR, then ligated into a different vector such as the GFP-containing vectors described above. To prepare a Tag-GFP polymerase recombinant fusion protein, vectors are constructed which contain sequences encoding the tag, GFP (wild-type or mutant), and the polymerase. The sequences are ordered to generate the desired Tag-GFP-polymerase recombinant fusion protein. Such methods are well known to those skilled in the art (Sambrook et al., Molecular Cloning, A Laboratory Manual, Cold Spring Harbor Laboratory, Cold Spring Harbor, N.Y., Chapter 17, 1989). This vector is expressed in bacteria such as *E. coli*, and the protein purified. The method of purification will depend on the affinity tag attached. Typically, the bacterial lysate is applied to a column containing a resin having high affinity for the tag on the fusion protein. After applying the lysate and allowing the tagged-fusion protein to bind, unbound proteins are washed away, and the fusion protein is subsequently eluted.

One of the most widely used tags is six or ten consecutive histidine (His) residues, which has high affinity for metal ions. A His-6 or His-10 moiety can be attached to GFP-polymerase by using pET vectors (Novagen, Madison, Wis.). The generation of GFP-His (Park and Raines, Protein Sci. 6:2344-9, 1997) and protein-GFP-His recombinant proteins have described previously (Prescott et al., FEBS Lett. 411: 97-101, 1997). The His-containing fusion proteins can be purified as described in Paborsky et al. (Anal. Biochem., 234:60-5, 1996). Briefly, the cell lysate is immobilized using affinity chromatography on Nit+-NTA-Agarose (QIAGEN, Valencia, Calif.). After washing away unbound proteins, for example using a buffer containing 8 mM imidazole, 50 mM Tris HCl, pH 7.5, 150 mM NaCl, the bound recombinant protein is eluted using the same buffer containing a higher concentration of imidazole, for example 100-500 mM.

The S-tag system is based on the interaction of the 15 amino acid S-tag peptide with the S-protein derived from pancreatic ribonuclease A. Several vectors for generating S-tag fusion proteins, as well as kits for the purification of S-tagged proteins, are available from Novagen (Madison, Wis.). For example vectors pET29a-c and pET30a-c can be used. The S-tag fusion protein is purified by incubating the cell lysate with S-protein agarose, which retains S-tag fusion proteins. After washing away unbound proteins, the fusion protein is released by incubation of the agarose beads with site specific protease, which leaves behind the S-tag peptide.

The affinity tag streptavidin binds with very high affinity to D-biotin. Vectors for generating streptavidin-fusion proteins, and methods for purifying these proteins, are described in Santo and Cantor (Biochem. Biophys. Res. Commun. 176: 571-7, 1991). To purify the fusion protein, the cell lysate is applied to a 2-iminobiotin agarose column, or another biotin-containing columns may be used, and after washing away unbound proteins, the fusion protein is eluted, for example with 6 M urea, 50 mM ammonium acetate (pH 4.0). The enzyme glutathione-S-transferase (GST) has high affinity for gluathione. Plasmid expression vectors containing GST (pGEX) are disclosed in U.S. Pat. No. 5,654,176 (Smith) and in Sharrocks (Gene, 138:105-8, 1994). pGEX vectors are available from Amersham Pharmacia Biotech (Piscataway, N.J.). The cell lysate is incubated with glutathione-agarose beads and after washing, the fusion protein is eluted, for example, with 50 mM Tris-HCl (pH 8.0) containing 5 mM reduced glutathione. After purification of the GST-GFP-polymerase fusion protein, the GST moiety can be released by specific proteolytic cleavage. If the GST-fusion protein is insoluble, it can be purified by affinity chromatography if the protein is solubilized in a solubilizing agent which does not disrupt binding to glutathione-agarose, such as 1% Triton X-100, 1% Tween 20, 10 mM dithiothreitol or 0.03% NaDodSO$_4$. Other methods used to solubilize GST-fusion proteins are described by Frangioni and Neel (Anal. Biochem, 210:179-87, 1993).

Recombinant GFP-Aequorin-Polymerase

Recombinant GFP-aequorin-polymerase can be generated using methods known to those skilled in the art, for example the method disclosed by Baubet et al. (Proc. Natl. Acad. Sci. USA 97:7260-5, 2000). Briefly, aequorin cDNA (for example Genbank Accession No. L29571), polymerase DNA, and a GFP plasmid are digested with the appropriate restriction enzyme(s) which allow for the insertion of the aequorin and polymerase into the MCS of a GFP plasmid in the sense orientation. The resulting fragments are ligated and expressed in bacteria, such as *E. coli*. The expressed recombinant GFP-aequorin-polymerase is then purified as described above. Affinity tags can also be added.

The ordering of the GFP, aequorin, and polymerase sequences can be optimised. The resulting GFP-aequorin-polymerases are tested to determine which has the optimal properties for sequencing. Such properties can include: ease of protein purification, amount of protein produced, amount of chemiluminescent signal emitted, amount of fluorescent signal emitted after excitation, minimal alteration of the fluorescent properties of the GFP and aequorin, and amount of polymerase activity Preparation of Nucleic Acid Molecule Template Primer Complex and Fixation to a Solid Substrate Preparation of Nucleic Acid Any source of deoxyribose nucleic acid oligonucleotides may be used in the sequencing reaction disclosed in this invention. Typically, these may be derived from genomic DNA which constitutes the major proportion of the nuclear compartment of cellular systems. Conveniently, the DNA is prepared by phenol or sodium perchlorate extraction (Forensic Sci Soc. 1994 October-December; 34 231-5.Ma H W, Cheng J, Caddy B.) In order to prepare manageable sized fragments suitable for sequencing, the genomic DNA is usually fractured by sonication or digested utilising a variety of endonucleases (Nucleic Acids Res. 1996, 24: 5026-5033).

An additional source of DNA utilised in the sequencing reactions is derived from mRNA which constitutes the ribonucleotide source within the cytoplasmic compartment of cellular systems. The mRNA is extracted, reverse transcribed to produce cDNA utilising reverse transcriptase and procedures for this purpose are available in kit form from numerous manufacturers, see Trizol RNA extraction (Invitrogen, Carlsbad, Calif.) and Reverse transcription (Gene Amp RNA-PCR Kit; Applied Biosystems, Foster City, Calif.) These kits are also used reverse transcribed DNA such that cDNA comprising nucleic acids with a common poly(A) 3' terminus and poly(T) 5' terminus are produced. Full protocols for this purpose have been previously described. (Ausubel F. M., Brent R., Kingston R. E et al. Calif. Tissue Int. 1995; 56 Suppl 1:S54-6).

In order to perform the sequencing reaction detailed in this disclosure, a template primer complex is formed. The region of the nucleic acid to be sequenced that will hybridise to a primer complementary to its sequence does not necessitate identification or introduction of a specific sequence since random primer sequences may be utilised. These random primers may also be used to expand the original DNA population prior to sequencing. (DNA Res. 2000 Feb. 28; 19-26. Nishigaki K, Akasaka K, Hasegawa A.)

Alternatively, each DNA strand may be ligated to a common sequence and a complementary common primer utilised to expand the global population of molecules in a manner representative in distribution to the original population (Tessier, D. C., Brousseau, R. and Vernet, T. (1986) Anal. Biochem. 158, 171-178). Alternatively a sequence common to and native to the DNA of interest may be used as a primer region.

Primer Attachment to Oligonucleotide and Approaches to Oligonucleotide Fixation to Solid Substrate There are two widely used methods for oligonucleotide attachment to a solid substrate. The first is the conjugation of a primer to the solid substrate followed by solid phase elongation of the primer when it is bound to a cognate template (Biotechniques 2002 February; 32(2):410, 412, 414-8, 420 Carmon A et al.). This approach will produce a complementary copy of the oligonucleotide under investigation bound to the matrix. In the second, the oligonucleotide may be directly derivitised with a residue reactive against the substrate or ligated to a DNA sequence containing the reactive group.

The most common methods involve either the prior ligation of DNA to a common motif that is derivatised with a reactive group at either the 5' or 3' terminus. Typically this will involve 5' aminated DNA to in conjunction aldehyde-modified surfaces. (Biochem Biophys Res Commun. 2003 Jan. 24; 300(4):915-20. Aoyagi K, et al) (Nucleic Acids Research, 2001, Vol. 29, No. 19 4062-4069 Valeri G. et al). Sequences containing such reactive groups at the 3' or 5' terminus suitable for ligation are commercially available and are produced by standard custom synthesis (Eurogenetics, Belgium, Invitrogen, CA).

The reactive groups may alternatively comprise biotin for binding to streptavidin derivatised plates, see Nucleic Acids Research, 2000, Vol. 28, No. 8 E33-00. Chandran R. Sabanayagam.

Typically, the ligated sequence is of such a length that it acts as both a common primer region in the sequencing reaction and also as a spacer such that when the oligonucleotide is attached to the solid surface by the reactive group at the terminus of the ligated sequence then the distance between the surface and the template region to be sequenced will allow the binding of a polymerase without steric hindrance. The length and nature of useful sequences has previously been described and is typically 30-50 angstroms in length. (Nicewarner Pena S R, et al; J Am Chem Soc. 2002 Jun. 26; 124(25):7314-23). The DNA is attached to a solid surface. The solid surface may be represented by but not limited to activated polystyrene or glass plates or microtitre wells or metal or polystyrene beads. Numerous methods are available for the attachment of DNA to a solid matrix and are described within the field of micro-array preparation, see for example Anal Biochem 2000 Apr. 10; 280(1):143-50 Zammatteo N et al. Where the oligonucleotide is directly bound to the solid support by the processes described above then it is considered as a template. The sequencing reaction is prepared by the addition of an excess of primer which is complementary to the ligated sequence. This is typically performed at a high temperature (85° C.) and the system is allowed to slowly cool.

An alternative methodology for the attachment of DNA sequencing complex to a solid support is to utilise a support derivatised with primer molecules. In this case, the primers may represent random sequences for attachment of global DNA as described by the manufacturer (NEB) and detailed elsewhere (Rothstein, J. D. et al. (1994) Proc. Natl. Acad. Sci. USA 91, 4155-4159) (Genome Res 2001 November; 11(11): 1926-34. Shapero M H et al) (Nucleic Acids Research, 2000, Vol. 28, No. 20 e87. Solid phase DNA amplification: characterisation of primer attachment and amplification mechanisms Celine Adessi, Gilles Matton, Guidon Ayala, Gerardo Turcatti, Jean-Jacques Mermod, Pascal Mayer and Eric Kawashima).

Alternatively, the primer may represent a sequence complementary to and common to all DNA molecules to be sequenced where the common sequence may be inherent to the DNA as exemplified by reverse transcribed mRNA using poly(T) primers or ligated to the DNA molecules. (Gene. 1990 Apr. 30; 89(1):117-22. Barringer K J, Orgel L et al) (J Biotechnol. 1994 Jun. 30; 35(2-3):229-38. Solid-phase cloning to create sublibraries suitable for DNA sequencing. Hultman T, Uhlen M., Royal Institute of Technology, Department of Biochemistry, Stockholm, Sweden. 5' ligation) (Proc Natl Acad Sci USA. 2000 Feb. 15; 97(4):1665-70. Brenner S, et al) (Nucleic Acids Research, 2000, Vol. 28, No. 20 e87 Céline Adessi et al), (Genome Res 2001 November; 11(11):1926-34 SNP genotyping by multiplexed solid-phase amplification and fluorescent minisequencing. Shapero M H, Leuther K K, Nguyen A, Scott M, Jones K W).

Attachment of Nucleic Acid to a Solid Substrate

Several methods for attaching nucleic acids (for example the sample nucleic acid to be sequenced or an oligonucleotide primer) to a substrate are available. In some embodiments, the nucleic acids can be attached by their 5' or 3' end, or anywhere in between. For example, a 5'biotinylated primer can be synthesized (Beaucage, Tetrahedron Letters 22:1859-62, 1981; Caruthers, Meth. Enzym. 154:287-313, 1987) and affixed to a streptavidin coated substrate surface (Hultman, Nucl. Acids Res. 17:4937-46, 1989). In another embodiment, the nucleic acid can be dried on amino-propyl-silanized (APS) glass, as described by Ha et al. (Proc. Natl. Acad. Sci. USA. 93:6264-68, 1996). In another embodiments, a silyl moiety can be attached to a nucleic acid, which can be used to attach the nucleic acid directly to a glass substrate, for example using the methods disclosed by Kumar et al. (Nucleic Acids Res. 28:e71, 2000). Briefly, silane is conjugated to a nucleic acid using the following method. Mercaptosilane [(3-Mercaptopropyl)-trimethoxysilane] is diluted to 5 mM stock solution with a reaction buffer such as sodium acetate (30 mM, pH 4.3) or sodium citrate (30 mM, pH 4). For conjugation of 5'-thiol-labeled nucleotides with mercaptosilane, 1 nmol nucleotides are reacted with 5 nmol mercaptosilane in 20 pl of the same buffer for 10-120 min at RT. The reaction mixture is used directly or diluted with the reaction buffer to a desired concentration for immobilization on a substrate, such as a glass microscope slide. 5'-acrylic-labeled oligonucleotides are conjugated to mercaptosilane using an identical procedure.

The 5'-thiol-labeled nucleotides are conjugated with aminosilane [(3-aminopropyl)trimethoxysilane] in dimethylsulfoxide (DMSO) in the presence of heterobifunctional linkers N-succinimidyl-3-(2-pyridyldithiol)-propionate (SPDP) or succinimidyl-6-(iodoacctyl-amino)hexanoate (SIAX). Nucleotides (final concentration 5-50 µM) are combined with 2.5 nmolaminosilane (added from 5 mM solution in ethanol) and 2.5 nmol bifunctional reagents (added from 5 mM stock solution in DMSO) in 10 µl DMSO, and the reaction allowed to proceed for 1-2 hours at RT.

Acrylic-labeled oligonucleotides (50-500 pmol) are combined with 25 nmol acrylicsilane (ymethacryloxy-propyl-trimethoxysilanc) in 10 µl of 30 mM NaOAc, pH 4.3. Ammonium persulfate (10% in $H_2O$) and N,N,N',N'-tetramethylethylenediamine (TEMED) are added to final concentration of 0.5 and 2%, respectively, and the mixture allowed to react for 30 minutes at RT.

After the conjugation reactions, the reaction mixture is referred to as silanized nucleic acid and can be directly used for spotting onto a substrate. Silanized nucleic acids can be spotted on the glass slides manually or with an automated arrayer (Genetic Microsystem, Woburn. USA). Nucleic acids in aqueous solutions can be kept in a humidified chamber for 15 minutes at RT after spotting onto the glass slide, dried at 50° C. for five minutes, dipped into boiling water for 30 seconds to remove non-covalently bound nucleic acids, and dried with nitrogen before hybridisation. Nucleotides in DMSO are left at RT for 15 minutes after spotting onto glass slides and dried at 50° C. for 10 minutes. These slides are sequentially washed with DMSO (3×2 min), ethanol (3×2 min) and boiling water (2 min) and dried with nitrogen for later use.

To hybridise a complementary nucleotide to the nucleotide attached to the substrate, such as an oligonucleotide primer, the nucleotide to be hybridised is diluted to between 20 nM and 1 μM in 5×SSC (750 mM NaCl, 125 mM sodium citrate, pH 7) with 0.1% Tween-20.

Hybridisation is done under cover slips in a humidifier at 37° C. for 30 minutes to overnight. Non-hybridised and non-specific nucleotides are removed by washing with 5×SSC containing 0.1% Tween-20 (3×1 min) followed by 1×SSC containing 0.1% Tween-20 (2×15 min).

If a longer nucleic acid molecule is hybridised, such as a sample nucleic acid, the hybridisation can be carried out at 65° C. for four hours in 3×SSC with 0.1% SDS and 1 μg/pl yeast tRNA. The slides are then washed with 1×SSC containing 0.1% SDS (3×2 min) and 0.1×SSC containing 0.1% SDS (3×5 min) at RT.

After washing, the slides can be dried with nitrogen gas. If repeated hybridisation on the same substrate is desired, the substrate is boiled in water for one minute then dried with nitrogen gas before proceeding to the next hybridisation reaction. To attach a nucleic acid by the 3' end, a terminal transferase can be used to "tail" the molecule.

In all the examples above the DNA bound to the solid surface constitutes the template. It is also possible to covalently attach patches of molecules derivatised with a reactive group at the 5' end and utilise these as primers in the sequencing reaction.

By using the methods described above, a solid surface is presented which constitutes single molecules of oligonucleotide attached to its surface in fixed positions (see FIG. 1) and/or where single molecules of different sequences are spread across the plate. Alternatively, the surface may constitute patches of molecules at fixed positions on the plate or micro array, each patch represented by clones of identical molecules (see FIG. 5). Alternatively beads may be presented and each bead is coated with a molecules derived from a single oligonucleotide clone.

The molecules may be covalently attached by their 3' terminus or non-covalently positioned with their 3' terminus in closest proximity to the surface by hybridising them to a primer molecule covalently attached to the matrix by its 5' terminus and has a sequence complementary to part of the oligonucleotide under investigation. Where the 3' end of the oligonucleotide is attached to the plate, the oligonucleotide is considered as a template for a polymerase and a primer complementary to a sequence on the oligonucleotide is added. It is feasible to utilise the 5' end of the oligonucleotide for attachment to the surface where the primer will be placed most distant to the surface and polymerisation will take place with elongation proximating towards the matrix.

The oligonucleotide or primer may contain a spacer proximal to the surface and a region common to or complementary to all oligonucleotides from which chain elongation may take place after the complementary DNA is added (Nicewarner Pena S R, Raina S, Goodrich G P, Fedoroff N V, Keating C D. Hybridisation and enzymatic extension of Au nanoparticle-bound oligonucleotides. J Am Chem Soc. 2002 Jun. 26; 124 (25):7314-23).

Where the polymerase is covalently attached to an intercalating dye such as Sybr-101, then in one embodiment (FIG. 1) competitive non-incorporable base specific nucleotide inhibitors are synthesized. The non-incorporated base analogues are designed in such a way that each analogue binds to the polymerase in a fashion complementary to one of the four bases present as the next base to be processed on the oligonucleotide.

Embedding Polymerase and Nucleic Acid in a Gel Matrix

As an alternative to attaching the polymerase or nucleic acid to a two-dimensional surface, the polymerase or nucleic acid may be embedded into a three-dimensional gel matrix. The polymerase or nucleic acid is added to the liquid matrix, which is allowed to solidify, trapping the polymerases or nucleic acids within it. Examples of this type of matrix include agarose and acrylamide, for example $Ni^{i+}$-NTA-Agarose (QIAGEN, Valencia, Calif.).

Preparation of Fluorescent Intercalating Dye and Fluorescent Quencher Labelled Inhibitors Preparation of Reactive Intercalating Dyes Intercalating dyes suitable for use in accordance with the present invention, and especially for making conjugates of an intercalating dye and DNTPs or DNTP analogues, are described in Svanvik et al (Analytical Biochemistry 281, 26-35 (2000), Light-Up Probes: Thiazole Orange-Conjugated Peptide Nucleic Acid for Detection of Target Nucleic Acid in Homogeneous Solution), Thompson & Woodbury (Biochemistry. 2000 Apr. 18; 39(15):4327-38. Fluorescent and photochemical properties of a single zinc finger conjugated to a fluorescent DNA-binding probe) and Privat et al (Photochem Photobiol. 2002 March; 75(3):201-10. Fluorescent properties of oligonucleotide-conjugated thiazole orange probes).

Preparation of Intercalating Dyes with Different Emission Wavelengths

There materials are particularly useful where more than one conjugate is employed, e.g. for methods of sequencing. Examples are disclosed in Benson et al (Nucleic Acids Res. 1993 Dec. 11; 21(24):5727-35 Related Articles-Heterodimeric DNA-binding dyes designed for energy transfer: synthesis and spectroscopic properties).

Further reactive esters of the intercalating dye thiazole orange:

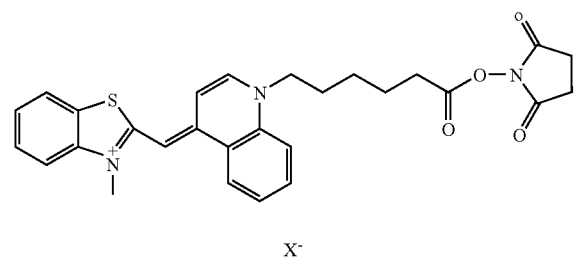

can be reacted with amino derivatised DNTPs at pH 8.

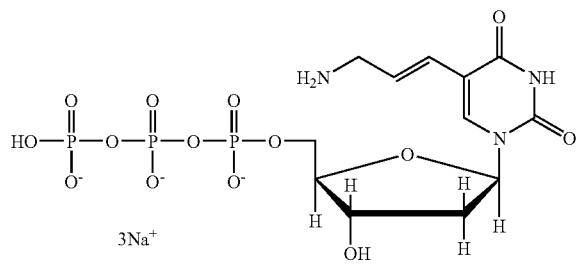

Amine derivatised DUTP

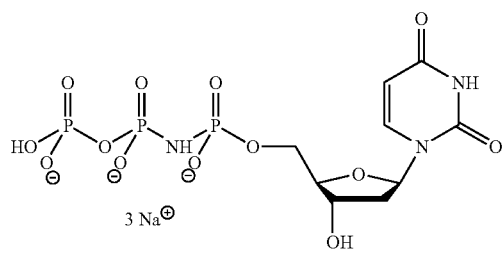

or non-incorporable Alpha-beta imino DNTP shown above) derivatised with amino linkers at the C5 position.

Chemical Synthesis of Intercalating Dye Bound DNA

The labelled primers described in this invention can potentially be synthesized independent of the action of polymerase starting with controlled pore glass supports (CPGs) having 5'-dimethoxytrityl-protected nucleosides with intercalating dye conjugate labelled bases, because conventional primer synthesis proceeds in the 3'-to-5' direction (thus only the four standard phosphoramidites would be required during synthesis). Alternatively, it is possible to synthesise primers using 3'-amino modifier CPGs (3'-amino-modifier C6 dC CPG and 3'-Amino-Modifier C6 dT CPG; Glen Research) followed by conjugation with the appropriate succinimidyl ester dye derivatives. One advantage to this two-step approach is the flexibility in the choice of fluorescent labels, because a large number of these are available commercially.

This is a description of the synthesis of nucleotide analogues that act as non-incorporable template dependent polymerase inhibitors. The labelling and synthesis of the non-incorporable analogues dNpCPP is described and can be applied to the synthesis of these analogues in relation to all four cognate bases. The synthesis relating to the incorporation of the methyl group between the alpha and beta phosphate is described in detail elsewhere and is referred here by way of reference (Hyman et al. (1995) J. Cell Biol. 128 (1-2):117.) (Hyman et al. (1992) Mol. Biol. Cell 3 (10):1155.)

Other inhibitors have been identified which may be labelled and the nature of these is referred to in detail elsewhere but inferred by way of reference (Nucleosides and Nucleotides 13(1-3), 339-350. 1994. Yanachkov and Wright G E) (Pharmacol Ther. 1990; 47(3):447-97. Wright G E, Brown N C. Deoxyribonucleotide analogs as inhibitors and substrates of DNA polymerases).

The addition of fluorescent molecules and quencher dyes to DNPCPP and related dNTP analogues is similar to those described for native DNTP and are well known to those skilled in the art. It is important that the nucleotide analogue maintains its cognition to the polymerase template-primer complex, but within this context they may be labelled utilising either the base, sugar or phosphate moieties as participants in the labelling reaction. Generally, methods are described for addition of labels to the base moiety. The details of synthesis are included herein by way of reference (Nucleic Acids Res. 2003 May 15; 31(10):2630-5. Giller G, et al.) (Chem Biol Interact. 1988; 66(1-2):85-100. Kelman D J, Lilga K T, Sharma M.) (J Biol. Chem. 1979 Dec. 10; 254(23): 12069-73. Yarbrough L R, Schlageck J G, Baughman M.)

The nucleotide moiety used may be modified by an amino allyl group such that after conjugation with the dye there is minimal impact on polymerase inhibitor interactions and fidelity of the interaction regarding the cognate template base. Dyes that are reactive to these amino allyl groups are usually modified with NHS ester or succinimidyl ester and are commercially available (Molecular Probes and Epoch Biosciences, Bothell, Wash.). The quencher NHS-ester is conjugated to the inhibitor as described by molecular probes and the modified analogue is purified by HPLC.

The use of a linker may allow the fluorophore orientation to be controlled, so that the optimal orientation for FRET or intercalation can be determined. An optimal orientation is one that generates the brightest emission signal without the nucleotide losing its ability to incorporate into the complementary nucleic acid strand. U.S. Pat. Nos. 5,047,519 and 5,151,507 to Hobbs et al teach the use of linkers to separate a nucleotide from a fluorophore. Examples of linkers may include a straight-chained alkylene, $C_1$-$C_{20}$, optionally containing within the chain double bonds, triple bonds, aryl groups or heteroatoms such as N, O or S. Substituents on the diradical moiety cainclude $C_1$-$C_6$ alkyl, aryl, ester, ether, amine, amide or chloro groups.

Where the spacer concerns the linkage between intercalating dye and a DNTP then the spacer may be designed to facilitate intercalation (Nucleic Acids Res. 1996 24 (5): 859-867 Bis-intercalation of a homodimeric thiazole orange dye in DNA in symmetrical pyrimidine-pyrimidine-purine-purine oligonucleotides. L F Hansen, L K Jensen, and J P Jacobsen)(Proc Natl Acad Sci USA. 1984 June; 81(11):3297-301. Nucleic acid-binding molecules with high affinity and base sequence specificity: intercalating agents covalently linked to oligodeoxynucleotides. Asseline U, Delarue M, Lancelot G, Toulme F, Thuong N T, Montenay-Garestier T, Helene C.) (Bioconjug Chem. 1993 September-October; 4(5):319-25. Oligonucleotide derivatives bearing reactive and stabilizing groups attached to C5 of deoxyuridine. Levina A S, Tabatadse D R, Khalimskaya L M, Prichodko T A, Shishkin G V, Alexandrova L A, Zarytova V P) and enable flexibility within the system in order to facilitate both intercalation as well as DNTP analogue insertion into the active site of the template-primer-polymerase complex. Where the intercalating dye conjugate is utilised for proof-reading dependent SNP analysis then the linker length should allow mismatched 3' termini which are bound to the dye to melt without limitation from the tether between the base and the dye.

When choosing acceptor fluorophores, it is preferred that the frequency used to excite the donor fluorophore on the polymerase does not overlap the excitation spectra of the acceptor fluorophores on the nucleotides. Each nucleotide should possess at least one acceptor fluorophore having an excitation spectrum which overlaps the emission spectrum of the donor fluorophore attached to the polymerase, such that the emission from the donor fluorophore excites the acceptor fluorophore.

When choosing fluorescent quencher dyes, it is also preferred that the emission spectra by the donor overlap with the absorption spectra of the quencher dye. Suitable donor fluorophore quencher combinations are provided by Molecular Probes, Epoch Biosciences, Amersham Biosciences and Eurogenetics. This overlap of spectra is not important where charge transfer dyes are utilized. Where the reaction is performed in solution bulk phase, rather than on a surface, then the use of charge transfer dyes may be preferable in order to limit absorption of the donor fluorescence in a fashion independent of the proximity of the dye quencher pair as this may happen at high quencher concentrations.

It is also important that the Forster distance between donor and acceptor or quencher is larger than the distance between the label on the polymerase and the label on the inhibitor. The Forster distance of numerous donor acceptor pairs are well known to those familiar with the art and have been published in tabular form by Molecular probes Incorporated. Where a polymerase is modified with a donor entity by reactive groups incorporated by site directed mutagenesis then these can be placed proximal to the DNTP binding site in order to preserve donor acceptor proximity but in a fashion that preserves polymerase integrity.

Where quencher dyes are coupled with the donor fluorophore then QSY (Molecular Probes) or BHQ (Epoch Biosciences and Amersham Biosciences) may be coupled with Alexa-488, FAM or Sybr 101 (Molecular Probes).

Detection Devices

Single Molecule Detection

Total Internal Reflectance (TIR) Fluorescence Microscopy

Figure 8:
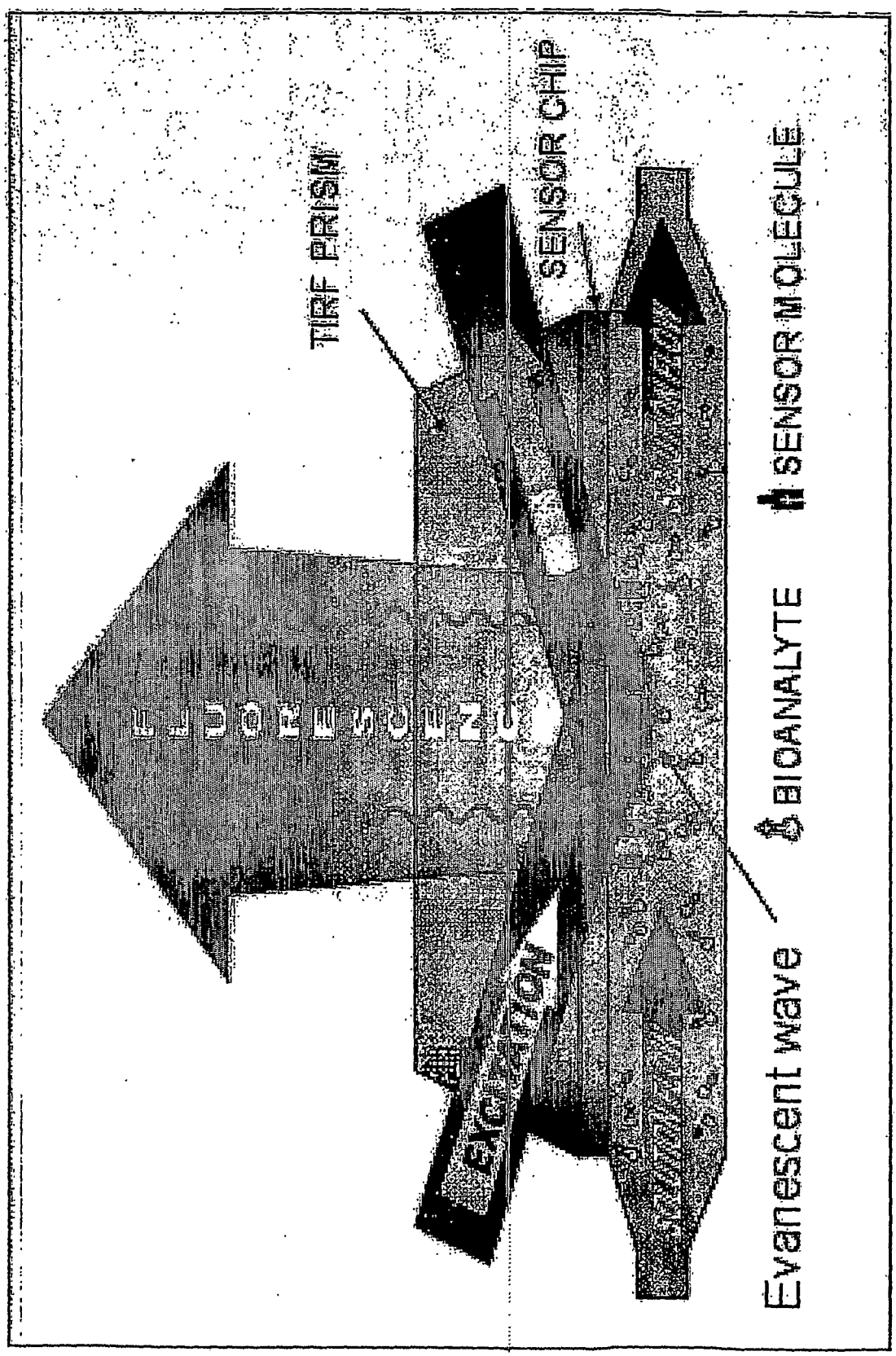
FIG. 8 is a schematic of a TIRF apparatus for oligonucleotide assessment.

Total internal reflectance (TIR) fluorescence microscopy can be used to detect the fluorescence produced in the methods of the present invention, for example using the methods and device described by Pierce et al (Nature, 388:338, 1997; Methods Cell Biol. 58:49, 1999); Funatsu et al (Nature, 374: 555, 1995); Weiss (Science, 283:1676, 1999) and Schutt et al (U.S. Pat. No. 5,017,009). An example of TIRF apparatus is shown in FIG. 8. The use of TIRF equipment for the detection of FRET or fluorescence quenching is well known in the art and is described in detail in Biophys J. 1999 February; 76(2): 709-15. Single-molecule imaging of RNA polymerase-DNA interactions in real timeshared Y, Funatsu T, Murakami K, Nonoyama Y, Ishihama A, Yanagida T.

TIRF is an optical phenomenon that occurs when light is directed at less than a critical angle, through a high refractive index material, toward an interface of that material with a second material having a lower refractive index. In this situation, all light is reflected back from that interface, except for a microscopic evanescent wave which propagates into the second material for only a short distance. In TIRF fluorescence microscopy, the first material is a glass substrate and the second material is water or another aqueous medium in which an assay is being conducted. When fluorescently labelled materials approach the interface, within the field of the evanescent wave, the fluorescent molecules can be energized and fluorescence detected which then emanates into the overlying solution. The advantage of TIRF is that it produces a superior signal-to-noise ratio, and reduces the photobleaching of the fluorescent molecules since only a thin layer of the sample is exposed. The technology herein is intrinsically protected to a significant degree from the effect of photobleaching. Although determination of a fluorophore bound to or proximal to a single molecule of DNA will be photobleached, in the context of this invention the fluorescent molecule is not necessarily covalently attached and as such is capable of molecular turnover being replaced by an unbleached molecule entering the reading focus from an unexcited plane.

Confocal Microscopy

To reduce photobleaching of the fluorophores, a confocal microscopy system can also be used in accordance with the present invention. An example of such a confocal laser is the Leica Confocal Spectrophotometer TCS-SP (Leica, Germany). The confocal laser can be used so that it only illuminates sequencing polymerases, leaving the remainder of the reservoir dark. To accomplish this, one can first scan the entire volume available for polymerases, and then program the microscope to only expose those small regions containing functioning polymerases. Another advantage of confocal microscopy is that sequencing reactions could occur in three dimensions. Confocal microscopy excludes planes that are not of interest, allowing one to increase the total number of sequences taken. This would allow more sequencing reactions to be performed and detected per field of view. The use of confocal microscopy for the detection of FRET or fluorescence quenching has previously been reported (.J Biotechnol. 2002 January; 82(3):211-31. Review. Dietrich A, Buschmann V, Muller C, Sauer M. Fluorescence resonance energy transfer (FRET) and competing processes in donor-acceptor substituted DNA strands: a comparative study of ensemble and single-molecule data (Methods. 2001 September; 25(1):78-86 Ha T. Single-molecule fluorescence resonance energy transfer).

Another way that can be used to reduce photobleaching is to incubate the sample in a solution containing an oxygen scavenger system, for example as described by Kitamura et al (Nature, 397:129, 1999); Okada and Hirokawa (Science, 283: 1152, 1999); Harada et al (J. Mol. Biol. 216:49, 1990). Examples of suitable solutions include: 1% glucose, 0.05 mg/ml glucose oxidase and 0.1 mg/ml catalase; and 0.5% 2-mercaptoethanol, 4.5 mg/ml glucose, 216 pg/ml glucose oxidase, 36 pg/ml catalase, 2 mM ATP in buffer.

Near-Field Scanning Optical Microscopy (NSOM)

Near-field scanning optical microscopy (NSOM) may also be used for the sequencing methods disclosed herein. Several methods and devices for NSOM have been described in the prior art, including U.S. Pat. No. 5,105,305 and PCT Publication WO 97/30366. In NSOM, an aperture having a diameter that is smaller than an optical wavelength is positioned in close proximity, i.e. within less than one wavelength, to the surface of a specimen and scanned over the surface. Light may be either emitted or collected by such an aperture in the end of a probe. Mechanical or piezoelectric means are provided for moving the probe relative to the sample. Light that has interacted with the sample is collected and detected by, for example, a spectrophotometer, and then a CCD camera. The strength of the detected light signal is typically stored, in the form of digital data, as a function of the probe position relative to the sample. The stored data can be converted into a nucleic acid sequence. NSOM allows optical measurements with sub-wavelength resolution, can measure FRET, and works well in solution (Ha et al, Proc. Nat. Acad. Sci. USA 93:6264-8, 1996). Standard microscopes can be converted to a near-field optical microscope using a device sold by Nanonics Ltd, (Malha, Jerusalem, Israel).

The advantage of NSOM is that high resolution of the sample can be obtained. However, since the probe scans the surface of the substrate, the number of sequencing reactions that can be monitored at any one time decreases. Kairos scientific provides a Fluorescence Imaging Micro Spectrophotometer (FIMS). This microscope generates a fluorescence emission spectrum for every pixel in the field of view. Therefore, a unique emission spectrum is generated for each nucleotide as it is added to the complementary nucleic acid strand.

In other embodiments, the method also allows for single molecule detection (SMD), for example using the system disclosed by Fang and Tan (Anal. Chem. 1999, 71:3101-5, herein incorporated by reference) Briefly, in this system an optical fibre is used to probe into a fluorophore solution, i.e. the aqueous environment 36 of FIG. 3, or at a solid surface, i.e. the substrate 12 shown in FIG. 3). The optical fibre has total internal reflection, allowing fluorescent molecules close to the surface to be excited by the evanescent wave. The fluorescent signals generated by the fluorophores are detected by an intensified charge-coupled device (ICCD)-based microscope system. Optical fibres can be purchased from Newport Corp, (Irvine, Calif.).

In yet further embodiments, SMD can be performed using the method disclosed by Unger et al (BioTechniques, 1999, 27:1008-14). Briefly, using a standard fluorescent microscope with mercury lamp excitation and a CCD camera, single fluorescent molecules can be observed in air and in aqueous solution, if the molecules are sufficiently separated by dilution.

Non Single Molecule Detection

Where patches of identical molecules are placed onto the surface of individual wells of a micro-titre plate then standard fluorescent plate readers may be used. These may excite and read from the transparent base of a black micro titre plate where the molecules are attached to the surface or by standard fluorometry where the reaction is performed in bulk solution, but only single nucleotide polymorphism measurements may be assessed rather than full sequencing.

Where patches of identical molecules are dispensed onto a glass surface then analysis may be performed utilising commercially available microarray readers, but only single nucleotide polymorphism measurements may be assessed rather than full sequencing. (Nucleic Acids Res. 1994 Oct. 11; 22(20):4167-75. Nikiforov T T et al). Another readout system applicable to the surface attachment of the nucleic acid molecules are microfluidic chips supplied and manufactured by a number of companies including Caliper Technologies, Aclara Biosystems, Cepheid, Inc., Fluidigm Corporation and Nanostream, Inc. The nucleic acid primers may be fixed to specific areas within channels comprising the chip such that additional components of the system or test samples may be applied. Where molecules are assessed in bulk fluid phase then any standard fluorometric reader may be used.

Sources of Electromagnetic Radiation

In particular embodiments, electromagnetic radiation can be emitted by a laser. The choice of laser used will depend on the specific donor fluorophore used. The wavelength of the laser light is selected to excite the donor fluorophore. For example, wild-type GFP and FITC can be excited by an argon laser at 488 run. To excite the H9-40 GFP mutant, blue laser diodes which emit at 400 nm (Nichia Chemical Industries Ltd.) or 404 nm (Power Technology Inc., Little Rock, Ak.) can be used. Other sources of electromagnetic radiation known by those skilled in the art can also be used, for example HeNe lasers and mercury lamps.

Fluidics

The use of a fluid handling system for carrying out the present invention is optional. For simplicity, one may prefer to add all of the necessary reagents, and then seal the chamber with a glass coverslip or a drop of oil to prevent desiccation. Alternatively, a slow flow of nucleotide/inhibitor/polymerase containing solution can be provided to replenish the nucleotides and to remove the products (diphosphate). Such a system would increase nucleotide use, but would maintain steady state conditions, which may increase the length of sequencing runs.

A computer chip that performs the liquid handling can be built that sits on the stage of a fluorescent microscope. Micromachine and microfluidic devices and methods for the dispensing of nanoliter size liquid samples has been previously described in the art (Service, Science 282:399-401, 1998; Burns et al. Science 282:484-7 1998). In one embodiment, a microfluidic device may be used for analysis of SNPs using single base assessment according to the present invention. By way of example, a microfluidic capillary or channel may be sectioned so that primers used for single base extension and for different SNP analysis are attached to beads and a partitioned in the capillary or channel. A DNA sample is added and flows along the capillary together with non-incorporable inhibitor-intercalate conjugates and polymerase. When these reagents reach the first bead and primer, the identity of a first SNP can be determined. The temperature can then be raised above the melting point of the primer and template and the sample is moved to the next bead for further processing, e.g. the detection of a second or subsequent SNP. In this embodiment, a second DNA containing may be added to the system by moving solutions through the capillary or channel, and in this fashion a plurality of sample DNAs and many SNPs may be assessed in a single system which can be reconstituted.

Detectors

A detector acts as the primary tool to capture the emission spectrums generated by the spectrophotometer. A CCD camera can be used as the detector to capture the image. The emission spectrums generated by the spectrophotometer are collected by the CCD camera, which converts this input into a charge. The charge is converted into a signal by the CCD output. The resulting signal is digitised, as a characteristic signal associated with each type of fluorophores. With colour CCD cameras containing more than 1000 by 1000 pixel fields (for example the Kodak Professional DCS 520 Digital Camera), or even 4096 by 4096 pixel fields (for example the Kodak 16.8i, KAF16800), it is possible to sequence as many as 1000 nucleic acids in parallel, at a rate of 360 bases per hour. If the templates are placed in a regular hexagonal regular array, about 17 pixels would be available for each molecule. Alternatively, monochrome CCD containing filters or other means of obtaining a spectrum may be used. As an alternative to a CCD camera, photomultiplier tubes or an intensified charge-coupled device (ICCD) can be used.

Assay Conditions and Buffers

Typically the inhibitors are added in molar excess over polymerase such that for each inhibitor 1-10 times the Kd value of each inhibitor is added. Typically this will be 20-100 uM, but will depend on the inhibitor and is generally in the range of the native substrate. (DNA Polymerase Structure and Mechanisms of Action. Manju M. Hingorani and Mike O'Donnell 2001). Typically, the polymerase is in molar excess over the template primer to the extent that the majority of template primer complex has a polymerase molecule attached. This is usually 10 times the Kd for the complex. Usually the polymerase will have a Kd of several nanomolar (Dzantiev, L. and Romano, L. J. J. Biol. Chem. 1999, 274, 3279), but this may vary depending on the enzyme used.

Buffers are used that are compatible with enzyme activity and are described by the supplier of the particular enzyme. The preferred enzymes, Sequenase, Thermosequenase and Klenow are available (Amersham Biosciences), and the Vent polymerase terminator is available from New England Biosciences) and will generally lack exonuclease activity. Calcium or magnesium ion concentration is titrated due to the disproportionate DNTP content in order to achieve optimal polymerase activity. Alternatively calcium can be replaced by manganese in order to achieve and optimal affinity between polymerase and inhibitor (PNAS USA. 1989 June; 86(11): 4076-80, Tabor S, Richardson C C).

The system may be heated in order to remove the DNA copy and the system can be sequenced again either to gain improved and confirmed data relating to a base that has already been assessed or in order to asses the position of one of the other four bases. When all four bases have been assessed then the average readout for each base can be overlaid with the other three bases assessed to give the complete sequence.

EXAMPLES

Example 1

A protocol for detecting SNPs using conjugates of a DNTP or DNTP analogue and an intercalating dye is shown in FIG. 13.

Materials

Lambda Exonuclease (Reactive against 5' phosphorylated DNA) (New England Biolabs), Therminator 9oN polymerase and Buffers (New England Biolabs, USA), Intercalator-Dye-DUTP conjugate (Custom Synthesised by Jena Biosciences, GmbH), Non-Incorporable DNTP; DUPNHPP (GmbH) and Pfu polymerase (Stratagene, Calif.).

A template which is representative of sample DNA was used having the sequence: 5'TGT CAC TCC TGA GCG ACG AAT CTG TAG ACC ACT TAT CCG TTT GCC TAT GCT (SEQ ID NO: 1).

Three first primers having sequences one base upstream of template base to be assessed) were as follows:

```
                                              (SEQ ID NO: 2)
a)    5'AGCATAGGCAAACGGATAAGTGG (Cognate to
      Adenosine)
a1)   dideoxy-terminated primer a)

(SEQ ID NO: 3)
b)    5'AGCATAGGCAAACGGATAAGT (cognate to Cytosine)
b1)   dideoxy terminated primer b)

(SEQ ID NO: 4)
c)    5'AGCATAGGCAAACGGATAAGTG (Cognate to Cytosine)
```

The second primer 2 was complementary to the first primer with additional single base addition to the 5' terminus. The 5'terminus was phosphorylated.
DATP; DTTP; DGTP; DCTP (New England Biolabs, USA)
DDATP; DDGTP; DDCTP; DDTTP (New England Biolabs, USA)
Stock Probe Preparation (Performed Once and Stored at −20° C.)

This reaction is shown in the top panel of FIG. 13.
(1) 20 uM of primer 1 and its cognate primer 2 were prepared in Therminator Buffer.
(2) The system was heated to 90° C. for 3 mins. and cooled to 55° C.
(3) Intercalator-Dye-DUTP conjugate was added to a concentration of 22 uM.
(4) 1 unit of Therminator polymerase/100 ul was added
(5) The system was incubated for 20 mins.
(6) The system was cooled to 37° C. and diluted $1/10^{th}$ in Lambda exonuclease buffer and 20 units of Lambda exonuclease/100 ul was added.
(7) The system was incubated for 1 hour at 37° C.
(8) The system was heated to 70° C. for 10 mins.
SNP Reaction
(1) Stock primer was diluted 1/10 (Final concentration 200 nM) in Pfu Buffer.
(2) Template was added to 100 uM (final concentration).
(3) The system was heated to 65° C. and Pfu Polymerase was added to a final concentration of 1 unit/100 ul.
(4) The system was incubated at 65° C. for 10 mins.

The results demonstrated that the system can detect the next base to be sequenced by using 3'-5'exonuclease.

|  | Incubation Time Mins | | | |
| --- | --- | --- | --- | --- |
|  | 0 | 6 | 16 | 42 |
| Primer 1a | 1479 | 1500 | 1545 | 1134 |
| Primer 1b | 1389 | 364 | 313.3 | 221 |
| Primer 1c | 1440 | 291.2 | 278.2 | 192.4 |

Example 2

Use of non-incorporable nucleotide triphosphates for SNP analysis and proof of principal for single molecule sequencing.
Materials
As example 1 above.
Method
(1) Dideoxy terminated primer and template were mixed at a ratio of 2:1 (final template concentrations were varied as shown)
(2) DGTP DCTP and DATP was added to a final concentration of 1 mM.
(3) 0.3 uM of Intercalator-Dye-DUTP conjugate was added to the system.
(4) In some samples non-incorporable DUTP (DUPNHPP) was added as shown.
(5) 300 nM Klenow exo- was added
(6) The system was heated to at 37° C.

Example 2a

These results demonstrate that the system can detect the next base to be sequenced and also its sensitivity to the non incorporable nucleotide family DNPNHPP. Where the intercalating dye is conjugated to DNPNHPP or other nonincorporable entities, then the dideoxy terminated primer is unnecessary and will allow sequential sequencing if a limited concentration of native bases are added. This experiment also demonstrates that the intercalating dye conjugate has minimal fluorescence unless template-primer and polymerase are present allowing homogenous protocols to be developed.

| Intercalate-Dye-DUTP | Buffer | T-P + Dye-DUTP | T-P + Dye-DUTP Primer-a1 | T-P + dye-DUTP Primer-b1 | T-P + Dye-DUTP + Primer1 + DUPNHPP |
| --- | --- | --- | --- | --- | --- |
| 75 | 66 | 183 | 1805 | 210 | 320 |

Example 2b

Buffer background subtracted. Results demonstrate that the system retains sensitivity as the concentration of DNA is reduced (towards single molecules)

|  | Template-primer-a concentration uM | | | | | |
| --- | --- | --- | --- | --- | --- | --- |
|  | 0.5 | 0.25 | 0.125 | 0.0625 | 0.03125 | 0.015625 |
| +Polymerase | 5100 | 2475 | 1259 | 616 | 320 | 150 |
| −Polymerase | 706 | 370 | 186 | 82 | 45 | 21 |
| +polymerase + DUpNHPP | 1802 | 916 | 438 | 234 | 114 | 55 |
| Signal: Background ratio | 7.2 | 6.6 | 6.7 | 7.6 | 7.1 | 7.1 |

All of the references mentioned herein are expressly incorporated by reference.

The invention claimed is:

1. A method for determining whether a template nucleic acid molecule comprises a specific complementary base in its sequence, the method comprising contacting the template nucleic acid molecule with a conjugate selected from the group consisting of (i) a deoxyribonucleotide triphosphate (DNTP) and an intercalating dye and (ii) a nucleotide analogue and an intercalating dye and determining whether the DNTP or nucleotide analogue is complementary to the specific complementary base in the template nucleic acid molecule sequence, said intercalating dye (a) being minimally fluorescent in the presence of single stranded DNA or in the absence of DNA, and, on binding to double stranded DNA, increases in fluorescence; or (b) on binding to double-stranded DNA shows a spectral shift.

2. The method of claim 1, further including formation of a complex, comprising said template nucleic acid molecule, a primer and a nucleic acid processing enzyme, the presence of said conjugate producing a signal in the presence of said complex, whereby a single base extension of said primer by said conjugate determines the identify of said specific complementary base.

3. The method of claim 1 which comprises employing a plurality of conjugates having different DNTP or nucleotide analogues that are complementary to different nucleotide bases, wherein the intercalating dyes of the different conjugates are capable of producing distinguishable signals.

4. The method of claim 1 which comprises employing a primer having a 3' end terminating one base upstream of the specific complementary base of the template nucleic acid sequence so that a single base extension of the primer by the conjugate determines the identity of the specific complementary base using the intercalating dye.

5. The method of claim 1, which comprises employing a conjugate comprising the DNTP or nucleotide analogue representing a single nucleotide base and adding unlabelled chain terminating bases representing the other three nucleotide bases to eliminate further primer extension.

6. The method of claim 1, wherein the specific complementary base is a single nucleotide polymorphism (SNP).

7. The method of claim 1 comprising repeating the method for sequencing the template nucleic acid molecule.

8. The method of claim 1, wherein the conjugate of the DNTP or nucleotide analogue is incorporable into the nucleic acid primer of a template-primer complex being extended by a nucleic acid processing enzyme.

9. The method of claim 1, wherein the DNTP or nucleotide analogue is non-incorporable into a nucleic acid primer being extended by a nucleic acid processing enzyme.

10. The method of claim 1, wherein the conjugate comprises a chain terminator DNTP or nucleotide analogue.

11. The method of claim 1, wherein the DNTP or nucleotide analogue is a nucleotide triphosphates of adenosine, thymine, cytosine, guanine or uracil.

12. The method of claim 8, wherein the DNTP or nucleotide analogue is an alpha-beta methylene derivative of a native DNTP.

13. The method of claim 1, wherein the intercalating dye is a DNA binding monomeric or multimeric asymmetric cyanine or acridine dye, propidium iodide, thiazole orange, ethidium bromide, ethidium monoazide, PO-PRO, BO-PRO, YO-PRO, TO-PRO, JO-PRO, LO-PR, BO-PRO, Hoechst 33258, Hoechst 33342, Hoechst 34580, 4',6-diamidino-2-phenylindole or 7-aminoactinomycin D (7-AAD).

14. The method of claim 1, wherein:
    (a) the intercalating dye is part of a label system which comprises a donor fluorophor and an acceptor fluorophor; or
    (b) the intercalating dye is part of a label system which comprises a fluorescent label and a quencher.

15. The method of claim 14, wherein the intercalating dye is a donor fluorophor.

16. A method for labelling a nucleic acid molecule in a template-primer complex using a nucleic acid processing enzyme, the method comprising contacting a conjugate selected from the group consisting of (i) a deoxyribonucleotide triphosphate (DNTP) and an intercalating dye and (ii) a nucleotide analogue and an intercalating dye in a template-primer complex with a nucleic acid processing enzyme and extending the nucleic acid molecule with the nucleic acid processing enzyme to label the nucleic acid molecule with the conjugate, said intercalating dye (a) being minimally fluorescent in the presence of single stranded DNA or in the absence of DNA, and, on binding to double stranded DNA, increases in fluorescence; or (b) on binding to double-stranded DNA shows a spectral shift.

17. The method of claim 16, wherein the conjugate of the DNTP or nucleotide analogue is incorporable into a nucleic acid primer of a template-primer complex being extended by a nucleic acid processing enzyme.

18. The method of claim 16, wherein the conjugate is a chain terminator DNTP or nucleotide analogue.

19. The method of claim 16, wherein the DNTP or nucleotide analogue is a nucleotide triphosphates of adenosine, thymine, cytosine, guanine or uracil.

20. The method of claim 16, wherein the intercalating dye is a DNA binding monomeric or multimeric asymmetric cyanine or acridine dye, propidium iodide, thiazole orange, ethidium bromide, ethidium monoazide, PO-PRO, BO-PRO, YO-PRO, TO-PRO, JO-PRO, LO-PR, BO-PRO, Hoechst 33258, Hoechst 33342, Hoechst 34580, 4',6-diamidino-2-phenylindole or 7-aminoactinomycin D (7-AAD).

21. The method of claim 16, wherein:
    (a) the intercalating dye is part of a label system which comprises a donor fluorophor and an acceptor fluorophor; or
    (b) the intercalating dye is part of a label system which comprises a fluorescent label and a quencher.

22. The method of claim 21, wherein the intercalating dye is a donor fluorophor.

23. The method of claim 16, which comprises contacting the enzyme-template-primer complex and the conjugates with one or more candidate inhibitors and determining whether one or more of the candidate inhibitors is an inhibitor of the enzyme or an inhibitor of the formation of enzyme-template-primer complex.

24. A method for determining the sequence of at least one nucleic acid base of a nucleic acid template molecule, wherein the at least one base is downstream of a 3' terminus of a primer which is annealed to the template forming a template-primer complex, the method comprising:
    (a) contacting the template-primer complex with (i) a nucleic acid processing enzyme capable of binding to the complex and having a binding site which is capable of binding a nucleotide triphosphate or an analogue thereof that is complementary to the template nucleic acid base that is being processed by the enzyme and (ii) one or more inhibitors of the nucleic acid processing enzyme, wherein the inhibitors are non-incorporable nucleotide analogues, so that a non-incorporable nucleotide analogue which is complementary to the downstream base of the template molecule binds to the nucleic acid processing enzyme; and (b) determining the identity of the non-incorporable nucleotide analogue and hence the sequence of the complementary base in the template nucleic acid molecule;

wherein the non-incorporable nucleotide analogue is selected from the group consisting of a conjugate which comprises a deoxyribonucleotide triphosphate (DNTP) and an intercalating dye and a conjugate which comprises a nucleotide analogue and an intercalating dye, said intercalating dye (a) being minimally fluorescent in the presence of single stranded DNA or in the absence of DNA, and, on binding to double stranded DNA, increases in fluorescence; or (b) on binding to double-stranded DNA shows a spectral shift.

25. The method of claim 24, wherein the method is repeated to sequence the nucleic acid template molecule.

26. The method of claim 24, wherein the method is used for sequencing a nucleic acid template molecule and the non-incorporable nucleotide analogues are employed in combination with native nucleotides, thereby allowing the enzyme to extend the primer and determine the sequence successive nucleotides.

27. The method of claim 24, wherein the method is used for determining whether a single nucleotide polymorphism (SNP) is present in the template nucleic acid molecule, and comprises selecting a primer which binds to the template upstream of a site of the SNP and determining the identity of the nucleotide at the site of the SNP.

28. The method of claim 10, wherein said chain terminator is selected from the group consisting of acyclo-DNTP or a dideoxy-DNTP or a 3'-OH modified DNTP or an alkyl or epoxy derivative of a 3'-OH modified DNTP.

29. The method of claim 18, wherein said chain terminator is selected from the group consisting of acyclo-DNTP or a dideoxy-DNTP or a 3'-OH modified DNTP or an alkyl or epoxy derivative of a 3'-OH modified DNTP.

* * * * *

UNITED STATES PATENT AND TRADEMARK OFFICE
CERTIFICATE OF CORRECTION

PATENT NO.        : 8,399,196 B2                                                    Page 1 of 1
APPLICATION NO.   : 10/546268
DATED             : March 19, 2013
INVENTOR(S)       : Mark J. Hoser It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2246 days.

Signed and Sealed this
First Day of September, 2015

Michelle K. Lee
*Director of the United States Patent and Trademark Office*